(12) United States Patent
Smakman et al.

(10) Patent No.: US 11,612,877 B2
(45) Date of Patent: Mar. 28, 2023

(54) MACROMOLECULAR COMPOSITIONS COMPRISING INDENE-DERIVATIVES, PREPARATION THEREOF, AND USE THEREOF

(71) Applicants: Stichting voor de Technische Wetenschappen, Utrecht (NL); Universiteit Utrecht Holding B.V., Utrecht (NL); UMC Utrecht Holding B.V., Utrecht (NL)

(72) Inventors: Robert Smakman, Nigtevecht (NL); Wilhelmus Everhardus Hennink, Utrecht (NL); Karin Gerarda Frederika Gerritsen, Utrecht (NL); Jacobus Adrianus Wilhelmus Jong, Utrecht (NL); Cornelus Franciscus van Nostrum, Utrecht (NL)

(73) Assignees: Stichting voor de Technische Wetenschappen, Utrecht (NL); Universiteit Utrecht Holding B.V., Utrecht (NL); UMC Utrecht Holding B.V., Utrecht (NL)

( * ) Notice: Subject to any disclaimer, the term of this patent is extended or adjusted under 35 U.S.C. 154(b) by 359 days.

(21) Appl. No.: 16/769,264

(22) PCT Filed: Dec. 4, 2018

(86) PCT No.: PCT/EP2018/083427
§ 371 (c)(1),
(2) Date: Jun. 3, 2020

(87) PCT Pub. No.: WO2019/110557
PCT Pub. Date: Jun. 13, 2019

(65) Prior Publication Data
US 2020/0368721 A1    Nov. 26, 2020

(30) Foreign Application Priority Data

Dec. 4, 2017    (EP) .................................... 17205273

(51) Int. Cl.
*B01J 20/26*    (2006.01)
*C08F 8/06*    (2006.01)
(Continued)

(52) U.S. Cl.
CPC ........... *B01J 20/261* (2013.01); *B01J 20/264* (2013.01); *B01J 20/267* (2013.01);
(Continued)

(58) Field of Classification Search
CPC .... B01J 20/2611; B01J 20/264; B01J 20/267; B01J 20/2805; B01J 20/3426;
(Continued)

(56) References Cited

U.S. PATENT DOCUMENTS

| 3,933,753 A | 1/1976 | Kuntz et al. |
| 4,178,241 A | 12/1979 | Sullivan et al. |

(Continued)

FOREIGN PATENT DOCUMENTS

| EP | 0121275 A1 | 10/1984 |
| WO | WO2004/078797 A1 | 9/2004 |

(Continued)

OTHER PUBLICATIONS

Smakman et al."Urea removal by means of direct binding", Clinical Nephrology, vol. 26,1986, pp.S58-S62. (Year: 1986).*
(Continued)

*Primary Examiner* — Michael M. Bernshteyn
(74) *Attorney, Agent, or Firm* — N.V. Nederlandsch Octrooibureau

(57) ABSTRACT

The present invention relates to a method for preparing a macromolecular composition comprising indene-deriva-
(Continued)

tives. The invention also relates to the macromolecular compositions per se, and to methods of using the macromolecular compositions. The macromolecular compositions are useful for undergoing subsequent reactions with small molecules.

7 Claims, 9 Drawing Sheets

(51) Int. Cl.
| | |
|---|---|
| *C08F 8/20* | (2006.01) |
| *B01J 20/28* | (2006.01) |
| *B01J 20/34* | (2006.01) |
| *C08F 212/32* | (2006.01) |
| *C08F 212/14* | (2006.01) |

(52) U.S. Cl.
CPC ....... *B01J 20/2805* (2013.01); *B01J 20/3425* (2013.01); *C08F 8/06* (2013.01); *C08F 8/20* (2013.01); *C08F 212/22* (2020.02); *C08F 212/24* (2020.02); *C08F 212/30* (2020.02); *C08F 212/32* (2013.01); *B01J 2220/445* (2013.01); *C08F 2800/10* (2013.01)

(58) Field of Classification Search
CPC . B01J 2220/445; C08F 212/24; C08F 212/30; C08F 212/32; C08F 212/22; C08F 8/06; C08F 8/20; C08F 2800/10
USPC .......................................................... 502/402
See application file for complete search history.

(56) References Cited

U.S. PATENT DOCUMENTS

| | | | | |
|---|---|---|---|---|
| 4,897,200 | A * | 1/1990 | Smakman | C08G 85/004 525/383 |
| 10,391,471 | B2 * | 8/2019 | Wendland | B01J 20/28057 |

FOREIGN PATENT DOCUMENTS

| | | |
|---|---|---|
| WO | WO2011/102807 A1 | 8/2011 |
| WO | WO2016/126596 | 8/2016 |
| WO | WO2017/116515 A1 | 7/2017 |

OTHER PUBLICATIONS

Robert Smakman et al:Urea removal by means of direct binding, Clinical Nephrology, vol. 26, Jan. 1, 1986 (Jan. 1, 1986), pp. S58-S62.
Smakman R et al: Promising In-Vitro 1-15 Results With a New Urea Sorbent, Life Support Sys, XX, GB, vol. 4, No. Suppl. 2, Jan. 1, 1986, pp. 264-266.
Marminon Christelle et al: "Microwave-assisted oxidation of indan-1-ones into ninhydrins", Tetrahedron Letters, vol. 56, No. 14, Feb. 28, 2015, pp. 1840-1842.
Hans-Dieter Becker et al.: Synthesis of Ninhydrin 1,2, Journal of Organic Chemistry, vol. 28, No. 7, Jul. 1, 1963, pp. 1896-1896.
Evenepoel, Pieter, et al. "Superior dialytic clearance of β2-microglobulin and p-cresol by high-flux hemodialysis as compared to peritoneal dialysis." Kidney international 70.4 (2006): 794-799.
Katritzky, Alan R., et al. "Quantitative measures of solvent polarity." Chemical reviews 104.1 (2004): 175-198.
Perl, Jeffrey, et al. "Changes in patient and technique survival over time among incident peritoneal dialysis patients in Canada." Clinical Journal of the American Society of Nephrology 7.7 (2012): 1145-1154.
Piraino, Beth, and Heena Sheth. "Peritonitis—Does Peritoneal Dialysis Modality Make a Difference?." Blood purification 29.2 (2010): 145-149.
Nesrallah, Gihad E., et al. "Intensive hemodialysis associates with improved survival compared with conventional hemodialysis." Journal of the American Society of Nephrology 23.4 (2012): 696-705.
Susantitaphong, Paweena, et al. "Effect of frequent or extended hemodialysis on cardiovascular parameters: a meta-analysis." American journal of kidney diseases 59.5 (2012): 689-699.
Ting, George O., et al. "Long-term study of high-comorbidity ESRD patients converted from conventional to short daily hemodialysis." American journal of kidney diseases 42.5 (2003): 1020-1035.
Gotch, Frank A. "Kinetic modeling of continuous flow peritoneal dialysis." Seminars in dialysis. vol. 14. No. 5. New York, US: Blackwell Science Inc, 2001.

* cited by examiner

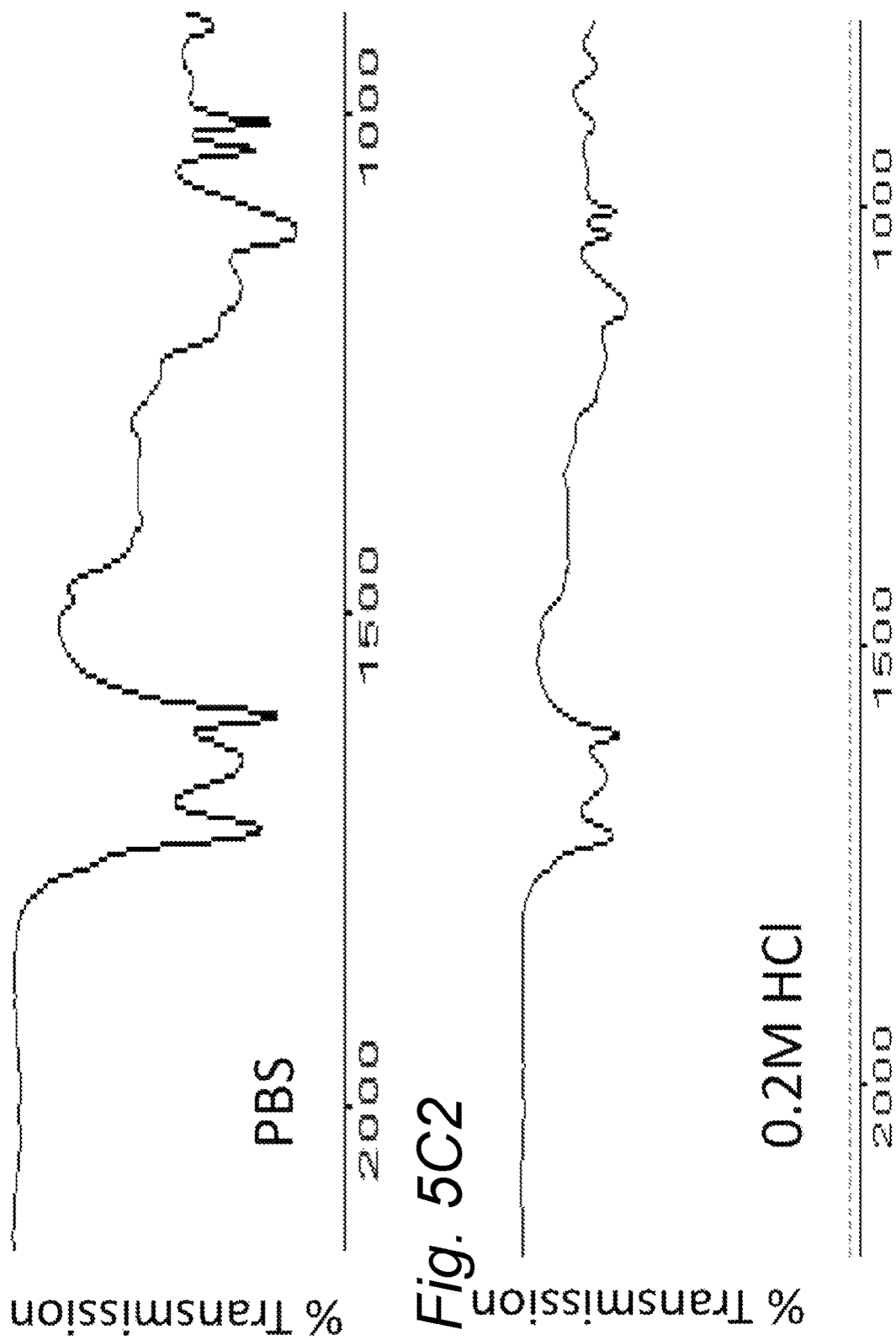

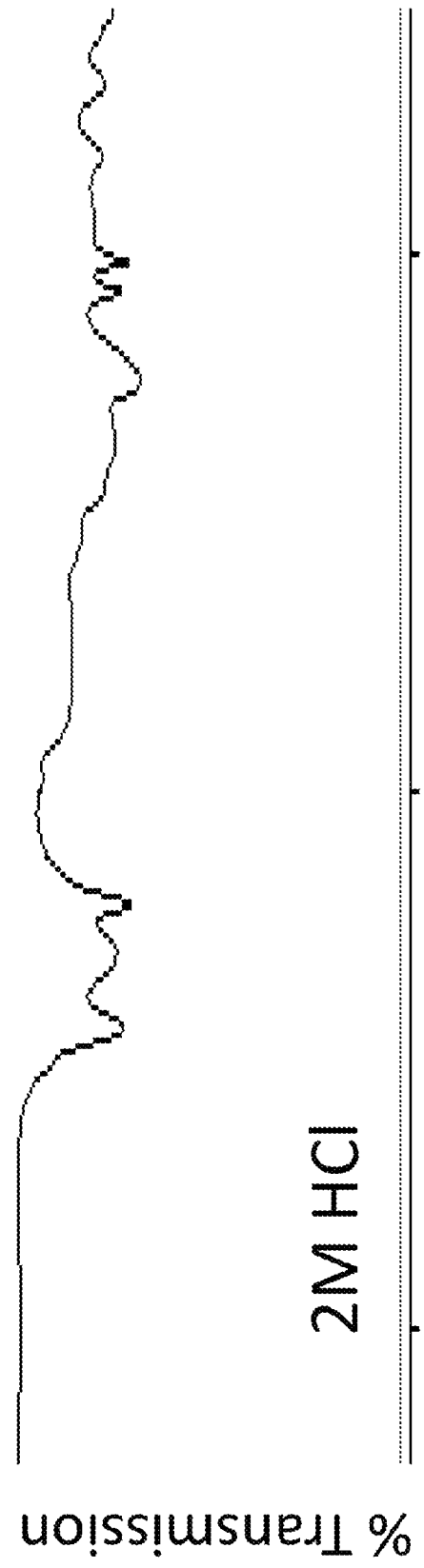
Fig. 5C3
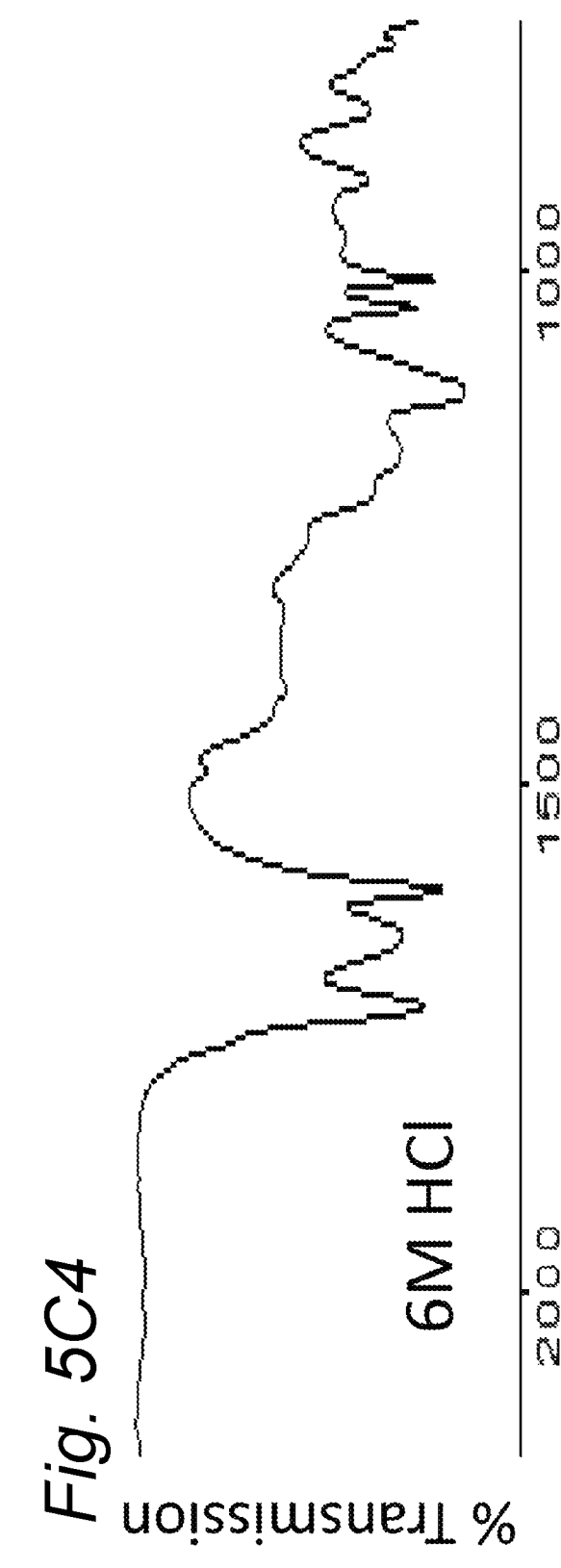
Fig. 5C4

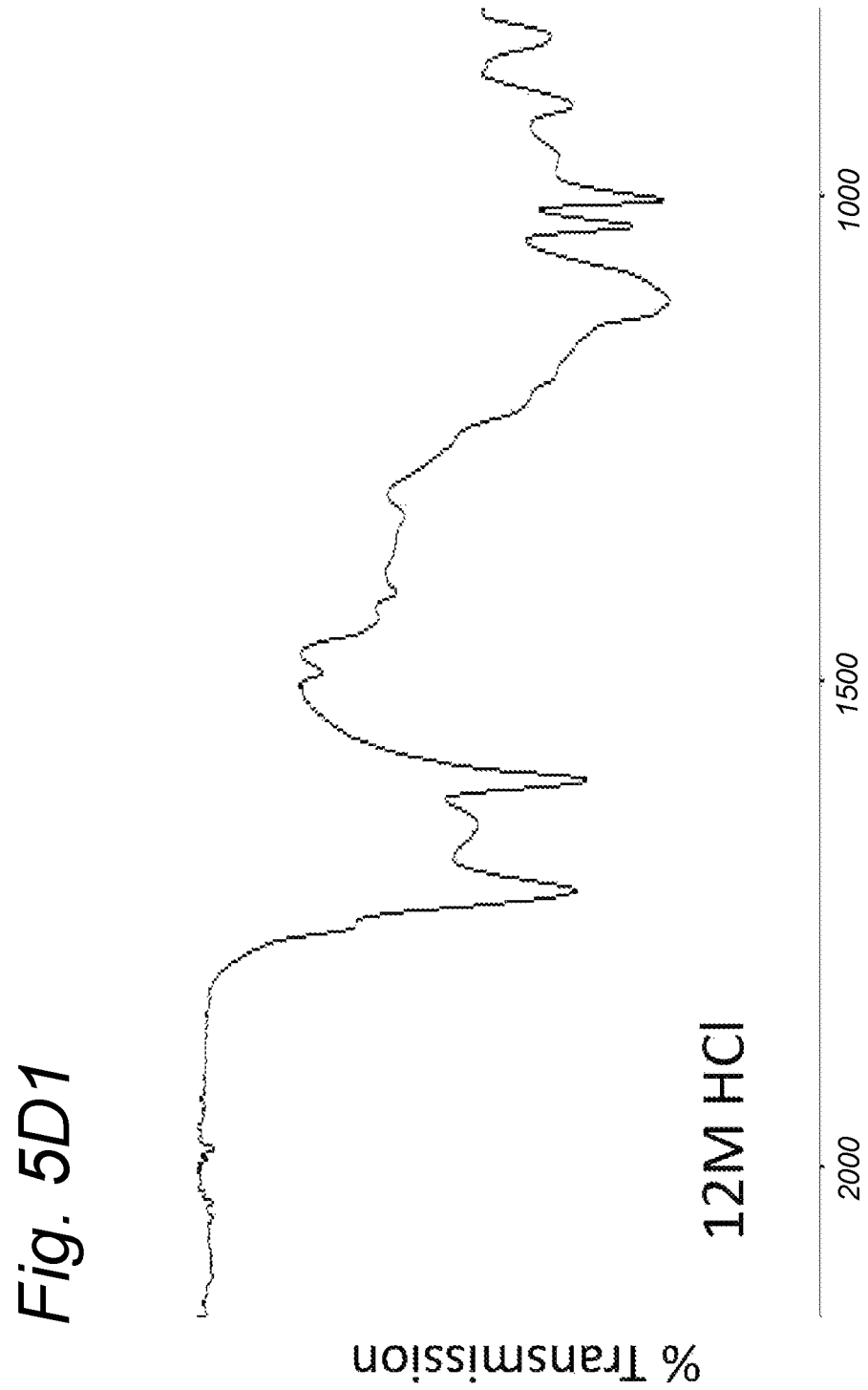
Fig. 5D1

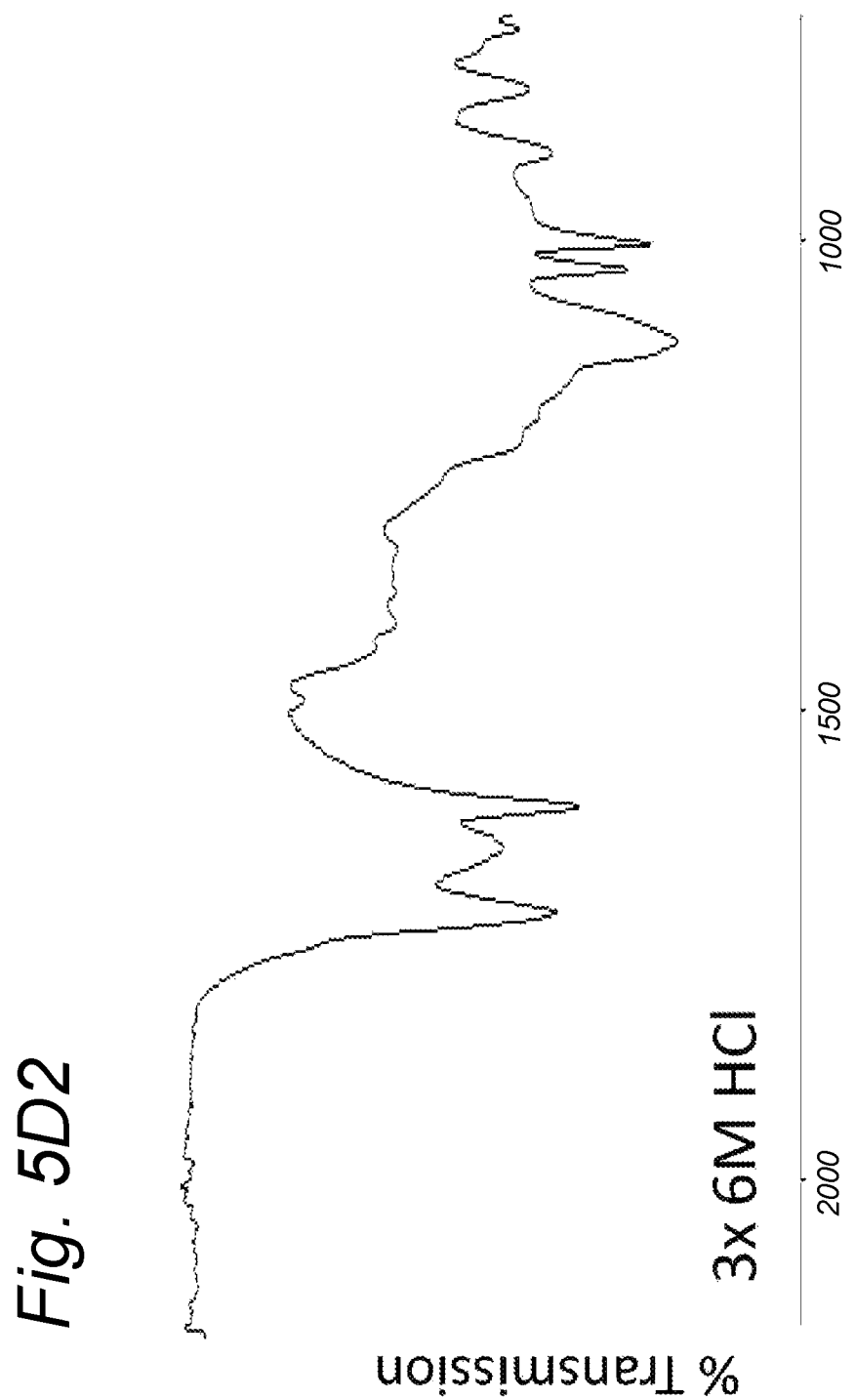
Fig. 5D2

MACROMOLECULAR COMPOSITIONS COMPRISING INDENE-DERIVATIVES, PREPARATION THEREOF, AND USE THEREOF

FIELD OF THE INVENTION

The present invention relates to a method for preparing a macromolecular composition comprising indene-derivatives. The invention also relates to the macromolecular compositions per se, and to methods of using the macromolecular compositions. The macromolecular compositions are useful for undergoing subsequent reactions with small molecules.

BACKGROUND ART

Patients with end stage kidney disease (ESKD) or severe acute kidney failure undergo dialysis (either hemodialysis, or HD, or peritoneal dialysis, or PD) to replace kidney function. Although lifesaving, conventional dialysis has major shortcomings. The treatment is time-consuming and removal of waste molecules and excess water is inadequate, contributing significantly to poor life quality, severe health problems and high mortality (15-20% per year). Treatment costs are very high.

In dialysis, patient fluids are generally dialysed against a dialysis fluid, which is then discarded. It is desirable to regenerate the dialysis fluid, to allow use of smaller volumes. In miniaturisation efforts, patient fluids are dialysed against a relatively small amount of dialysis fluid, referred to as dialysate. During this process waste solutes from the patient fluid move towards the dialysate by diffusion and/or convection, often through a membrane such as a semipermeable membrane. If waste solutes are later removed from a dialysate, it can be reused, which is referred to as regeneration of dialysate. Efficient regeneration of dialysate would reduce the need for large volumes of dialysis fluid, making dialysis more practically implemented, less resource-dependent, and reducing waste streams.

A miniature artificial kidney device will be a major breakthrough in renal replacement therapy. Worldwide the number of dialysis patients has been estimated at 2.5 million (see vision-fmc.com/files/pdf_2/ESRD_Patients_2012.pdf). Currently, approximately 85% of the dialysis patients uses HD techniques, either in a center (>96%) or at home (<4%) (see the ERA-EDTA Registry Annual Report 2012). While in-center HD requires long frequent visits to the hospital (about 3 times per week, 4 h per session), home HD offers more flexibility and autonomy. However, home HD still requires bulky dialysis machines and a large supply of dialysis fluids (at least 20 L per treatment) or a bulky immobile water purification system. A user-friendly lightweight HD device that is independent of a fixed water supply or large supply of dialysis fluids will increase patients' mobility allowing them to stay active in social life and travel freely.

The large fluctuations in water balance and uremic toxin levels between dialysis treatments with standard thrice weekly HD could be attenuated with continuous or more frequent HD, which may improve patient outcome (Nesrallah 2012; Ting 2003; Susantitaphong 2012). A more liberal diet would be allowed. Significant cost reductions will be achieved through reduced need of dialysis personnel and related infrastructure, fewer medications and less hospitalizations due to reduced comorbidity.

PD is currently used by approximately 15% of the dialysis patients (ERA-EDTA Registry Annual Report 2012). Although PD, in contrast to HD, offers the opportunity to dialyze continuously, the technique has some major drawbacks: uremic toxin clearance is low (Evenpoel 2006), exchange procedures are time-consuming and technique failure rate is high (median technique survival is 3.7 years) due to high incidence of infection of the peritoneal membrane (peritonitis) and membrane failure (Perl 2012). The low dialysis efficacy is largely due to fast dissipation of the concentration gradient between plasma and peritoneal dialysate during a dwell, thereby limiting solute transport (Gotch 2001). A miniature PD device that continuously regenerates the dialysate, thereby maintaining the plasma-dialysate concentration gradient, would greatly enhance PD efficacy. This will allow reduction in the number of time consuming exchanges while still improving waste solute clearance. In addition, reducing the number of connections decreases the risk of contamination and will lower peritonitis rates (Piraino 2010; De Fijter, 1991). Continuous glucose infusion by the miniature PD device will reduce functional deterioration of the peritoneal membrane by avoiding very high toxic glucose concentrations as applied in conventional PD (Gotch 2001). By preventing the two major causes of technique failure in conventional PD (recurrent infection and functional loss of the peritoneal membrane) the miniature artificial kidney will significantly prolong technique survival.

A user-friendly wearable or portable dialysis device, providing dialysis outside the hospital, would thus represent a huge leap forward for dialysis patients and would significantly increase their quality of life. The device would allow continuous or more frequent dialysis which will improve removal of waste solutes and excess fluid, and hence patient health. A miniaturized design, independent of a fixed water supply, offers freedom and autonomy to the patient.

In recent years, small prototype dialysis devices have been constructed that adequately remove some organic waste solutes and waste ions. However, thus far no adequate strategy for removal of urea exists, while urea is one of the main obstacles for successful realization of a miniature artificial kidney device. Urea is the waste solute with the highest daily production (as primary waste product of nitrogen metabolism) and exerts toxic effects at high plasma concentrations. However, urea is difficult to bind and has low reactivity.

EP121275A1/U.S. Pat. No. 4,897,200A discloses a ninhydrin-type sorbent that is formed out of a polymerized styrene composition in a six-step synthetic sequence. A urea binding capacity of 1.2 mmol/g dry sorbent in 8 hours was shown at clinically relevant urea concentrations. However, for effective miniaturisation, a higher urea binding capacity is required.

DE2305186A1/U.S. Pat. No. 3,933,753A discloses a macromolecular composition wherein a polystyrene-like scaffold is post-modified to comprise glyoxal moieties, reaching a conversion of 0.72 glyoxal moieties per monomer in the composition. This composition could not capture more urea than 1 mmol/g, and it was shown to be more suitable for the removal of aniline, which is not clinically relevant. Glyoxal moieties do not form hemiaminal moieties upon reaction with urea, but instead form imidazole-type moieties that can react with an additional free glyoxal. Also, aldehydes comprised in the glyoxal are intrinsically less stable than ninhydrin. WO2004078797A1 discloses similar keto-aldehyde materials, reaching a urea binding capacity of 1.5 mmol/g.

U.S. Pat. No. 4,178,241A discloses a polystyrene-based material comprising para-thio, para-nitro, or para-amino moieties. Only for thio moieties, the binding of urea was again shown to be at about 1.5 mmol/g. Other functional groups performed less well. On the other hand, creatinine was shown to be bound at well over 90% of normal adult daily production for each functional group.

WO2017116515A1 discloses the use of electrically charged membranes to improve urea separation from a dialysis fluid, and suggests the use of electrooxidation of separated urea. A disadvantage of this method is that reactive oxygen species are generated as a byproduct.

WO2011102807A1 discloses epoxide-covered substrates. The epoxides can be used to recover solutes from a solution. They are also used to immobilise urease enzymes, which help dispose of urea. A disadvantage of urease enzymes is their sensitivity to environmental factors, their costly and laborious production, and the fact that ammonium is generated by their reaction, which in turn requires removal using cation exchangers comprising toxic materials such as zirconium phosphate. WO2016126596 also uses a very different substrate, viz. reduced graphene oxide. While a high urea binding capacity was shown, the captured urea represented less than 15% of the initial urea concentration.

To enable the development of improved artificial kidney devices, there is an ongoing need for easily prepared sorbents that bind higher amounts of urea without the risk of leaching components into a dialysate, and without generating harmful side products.

SUMMARY OF THE INVENTION

In a first embodiment of its first aspect, the invention relates to a method for producing a ninhydrin-type sorbent, comprising the steps of:
i) providing a monomer of general formula (I):

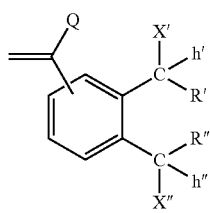

wherein:
Q is —H or —$CH_3$;
h' and h" are each independently absent or chosen from a halogen and —H;
X' and X" are each independently chosen from a halogen, —H, =O, =N—$(CH_2)_n$—H, —O—$(CH_2)_n$—H, —O—C$(CH_3)_3$, —O—CH$(CH_3)_2$, —$(CH_2)_n$—H, and —N(—$[CH_2]_n$—H)$_2$, wherein any —H may be optionally replaced by a halogen, wherein each instance of n is independently chosen from 0, 1, 2, 3, or 4,
R' and R" are each independently chosen from a halogen, —H, —OH, —O—$(CH_2)_n$—H, —O—C$(CH_3)_3$, —O—CH$(CH_3)_2$, —N(—$[CH_2]_n$—H)$_2$, and —$(CH_2)_n$—H, wherein any —H may be optionally replaced by a halogen, wherein each instance of n is independently chosen from 0, 1, 2, 3, or 4, or wherein R' and R" together form a bridging moiety selected from —$CH_2$—, =CH—, —C(=O)—, —C(—OH)$_2$—, —C(—OH)$_2$—C(—OH)$_2$—, —O—, —NH—, and —C(h''')(X''')—, wherein
h''' is independently chosen as defined for h' or is —NH—C(=O)—$NH_2$;
X''' is independently chosen as defined for X'; or wherein X''' is —OH and h''' and one of h' or h" together form a bridging moiety —NH—C(=O)—NH—; and
ii) polymerizing the provided monomer to obtain a polymer; and
iii) converting polymerized monomers of general formula (I) that are not ninhydrin-type monomers into ninhydrin-type monomers.

In an embodiment of the first aspect, the invention provides a method as described above, wherein a comonomer is provided along with the monomer of general formula (I). In a further embodiment of the first aspect, the invention provides the method as described above, wherein the polymer is crosslinked after polymerization or during polymerization.

In an embodiment of the first aspect, the invention provides the method as described above, wherein in step iii) a conversion reaction is used comprising a step selected from the group consisting of: a) oxidation, preferably using an oxide such as $SeO_2$; b) halogenation, preferably using $Br_2$, $Cl_2$, or $I_2$; c) alkylation, preferably using dimethyl sulfoxide (DMSO) or ethyl acetoacetate; d) fragmentation, preferably by heating to about 80° C.; and e) hydrolysis, preferably by heating to about 80° C. in an aqueous environment.

In an embodiment of the first aspect, the invention provides the method as described above, wherein in step iii) more than 30% of the monomers of general formula (I) are converted into ninhydrin-type monomers. Further embodiments exist within this aspect.

In a second aspect, the invention provides the ninhydrin-type sorbent obtainable by the method according to the first aspect, wherein the sorbent has a urea binding capacity of more than 1.4, preferably of more than 2.1 mmol urea per gram of sorbent. In a second embodiment of the second aspect, the invention provides a ninhydrin-type sorbent according to the first embodiment of the second aspect, wherein at least 30% of the polymerized monomers is a ninhydrin-type monomer. In a third embodiment, the invention provides a composition comprising the ninhydrin-type sorbent of the second aspect and a pharmaceutically acceptable excipient. In a fourth embodiment within this aspect, the ninhydrin-type sorbent is comprised in a cartridge for use in a dialysis device. In a fifth embodiment within this aspect, the ninhydrin-type sorbent is comprised in a dialysis device. Further embodiments exist within this aspect.

In a third aspect, the invention provides the ninhydrin-type sorbent according to the second aspect, or composition according to the second aspect, for use as a medicament, preferably for use in the treatment of a disease or condition associated with accumulation of urea.

In a fourth aspect, the invention provides a method for removing nucleophilic waste solutes from a fluid, comprising the steps of: i) providing a fluid comprising nucleophilic waste solutes, and iia) contacting said fluid with a ninhydrin-type sorbent as defined in the second aspect, or with a composition as defined in the second aspect, or alternately iib) contacting said fluid with a dialysis fluid through a membrane, wherein the dialysis fluid is in contact with a ninhydrin-type sorbent as defined in the second aspect, or with a composition as defined in the second aspect, and iii) optionally, recovering the fluid.

In a fifth aspect, the invention provides a method for regenerating a ninhydrin-type sorbent as defined in the second aspect, or a cartridge as defined in the second aspect, comprising the steps of: i) contacting the ninhydrin-type sorbent with an acidic regeneration solution; and ii) optionally, heating the regeneration solution while it is in contact with the ninhydrin-type sorbent; and iii) recovering the ninhydrin-type sorbent from the regeneration solution; and iv) optionally, washing the ninhydrin-type sorbent.

DESCRIPTION OF EMBODIMENTS

The present invention seeks to provide an improved ninhydrin-type sorbent with an increased capacity for nucleophilic waste solutes, of which urea is an important example. A sorbent is a material that binds target substances—in this case the sorbent binds nucleophiles such as urea. The inventors invented macromolecular polycarbonyl compounds with high urea binding capacity and fast binding kinetics, rendering the materials suitable for use as sorbents. The improved sorbent allows for the miniaturisation of sorbent cartridges and is thus an important step towards a miniature artificial kidney device.

The sorbent can advantageously be used in (hemo)dialysis for the removal of urea, wherein blood is led past a membrane such as a semipermeable membrane that separates it from a small amount of dialysis fluid. The sorbent then binds nucleophilic waste solutes such as urea, so that diffusion of these solutes over the semipermeable membrane is continued and does not slow down due to saturation.

Because effective urea removal is crucial for successful dialysate regeneration, an object of the present invention is to provide sorbents with high binding capacity, suitable for application in a miniature artificial kidney device, for example by preparing cartridges loaded with the sorbent. Another object of the invention is to provide a method for producing such an improved sorbent, preferably in a cost-effective matter by using low-cost reactants, thus allowing a reduction in the cost of healthcare. Another object of the invention is to provide a method wherein such sorbents, compositions, or cartridges are used to remove nucleophilic solutes such as urea from a solution.

The inventors have surprisingly found that an improved ninhydrin-type sorbent can be formed by polymerizing precursor monomers, and by subsequent conversion of these polymerized precursor monomers into ninhydrin monomers. In the state of the art, ninhydrin is formed based on styrene. The invention uses monomers that are structurally more close to ninhydrin, such as vinyl-indene or vinyl-indanone Surprisingly, the sorbents formed by the method of the invention have an improved capacity for binding urea, and thus allow improved methods for their use.

The inventors surprisingly found that improved ninhydrin-type sorbents can be obtained by using precursor monomers that resemble ninhydrin more closely than styrene does. As part of the invention a family of suitable precursor monomers was found. Accordingly, in a first aspect, the invention provides a method for producing a ninhydrin-type sorbent, comprising the steps of:

i) providing a monomer of general formula (I):

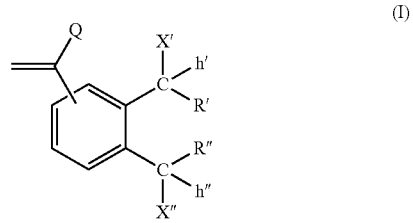

wherein:
Q is —H or —CH$_3$;
h' and h" are each independently absent or chosen from a halogen and —H;
X' and X" are each independently chosen from a halogen, —H, =O, =N—(CH$_2$)$_n$—H, —O—(CH$_2$)$_n$—H, —O—C(CH$_3$)$_3$, —O—CH(CH$_3$)$_2$, —(CH$_2$)$_n$—H, and —N(—[CH$_2$]$_n$—H)$_2$, wherein any —H may be optionally replaced by a halogen, wherein each instance of n is independently chosen from 0, 1, 2, 3, or 4,
R' and R" are each independently chosen from a halogen, —H, —OH, —O—(CH$_2$)$_n$—H, —O—C(CH$_3$)$_3$, —O—CH(CH$_3$)$_2$, —N(—[CH$_2$]$_n$H)$_2$, and —(CH$_2$)$_n$—H, wherein any —H may be optionally replaced by a halogen, wherein each instance of n is independently chosen from 0, 1, 2, 3, or 4, or wherein R' and R" together form a bridging moiety selected from —CH$_2$—, =CH—, —C(=O)—, —C(—OH)$_2$—, —C(—OH)$_2$—C(—OH)$_2$—, —O—, —NH—, and —C(h''')(X''')—, wherein
h''' is independently chosen as defined for h' or is —NH—C(=O)—NH$_2$;
X''' is independently chosen as defined for X'; or wherein X''' is —OH and h''' and one of h' or h" together form a bridging moiety —NH—C(=O)—NH—;
ii) polymerizing the provided monomer to obtain a polymer; and
iii) converting polymerized monomers of general formula (I) that are not ninhydrin-type monomers into ninhydrin-type monomers.

Such a method is hereinafter referred to as a production method according to the invention. A ninhydrin-type sorbent obtainable by a production method according to the invention is hereinafter referred to as a ninhydrin-type sorbent according to the invention.

Ninhydrin-Type Sorbent

A sorbent is a material that is designed to bind, absorb, or adsorb other substances. Sorbents for binding nucleophilic waste solutes are known in the art, and have already been described for use in hemodialysis devices (EP121275A1). In the context of this invention, a sorbent is a macromolecular composition that is a solid, a suspended solid, a colloidal suspension, an aggregate, a resin, or a polymer that can be dissolved or partially dissolved. It can bind nucleophilic waste solutes, after which the sorbent can be recovered from a mixture. The binding can be covalent, or non-covalent such as via electrostatic interactions or via hydrophobic interactions. Preferably the binding of a nucleophilic waste solute by a sorbent is covalent.

A ninhydrin-type sorbent is a sorbent that comprises ninhydrin-type moieties. Ninhydrin is 2,2-dihydroxy-1H-indene-1,3(2H)-dione, and is also known as 2,2-Dihydroxy-indane-1,3-dione and 1,2,3-Indantrione hydrate. A ninhydrin-type moiety is preferably a hydrate of a five-membered ring-structure with three vicinal carbonyl groups, anellated to two adjacent positions of an aromatic ring or aromatic ring-system, preferably anellated to a phenyl moiety. Preferred examples of ninhydrin-type moieties are selected from the group consisting of 4-[2,2-dihydroxy-1H-indene-1,3(2H)]-dionyl, 5-[2,2-dihydroxy-1H-indene-1,3(2H)]-dionyl, 6-[2,2-dihydroxy-1H-indene-1,3(2H)]-dionyl, and 7-[2,2-dihydroxy-1H-indene-1,3(2H)]-dionyl. More preferred ninhydrin-type moieties are selected from the group consisting of 5-[2,2-dihydroxy-1H-indene-1,3(2H)]dionyl and 6-[2,2-dihydroxy-1H-indene-1,3(2H)]dionyl. Ninhydrin has an axis of symmetry, so that 5-[2,2-dihydroxy-1H-indene-1,3(2H)]dionyl and 6-[2,2-dihydroxy-1H-indene-1,3(2H)]-dionyl are identical if no other substituents are present. Numbering of ninhydrin positions is shown below, with numbering of the monomer of general formula (I) shown for reference.

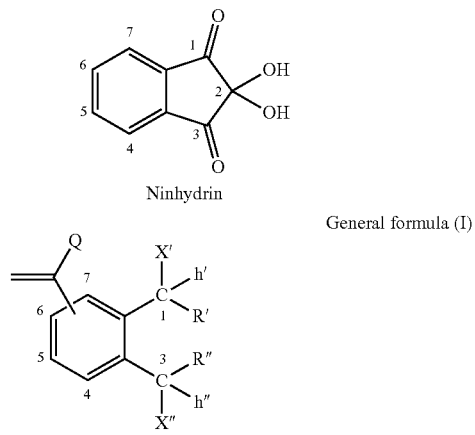

Ninhydrin-type sorbents according to the invention are suitable for binding nucleophilic waste solutes. These solutes react with the ninhydrin-like moieties comprised in the sorbent. Accordingly, in a second aspect the invention provides a ninhydrin type sorbent according to the invention, obtainable by a production method according to the invention, wherein the sorbent has a urea binding capacity of more than 1.4, preferably of more than 2, 1 mmol urea per gram of sorbent.

Urea is a small, highly polar molecule that, by virtue of its polarity and capability to participate in hydrogen bond formation, is highly soluble in water (>400 mg/ml) and in protic organic solvents such as methanol, ethanol, and glycerol. While the role of urea in biochemistry is essential, and it is an important molecule industrially, including as a source of nitrogen for fertilizer and as a polymer precursor, it is often important for urea to be removed from fluid solutions.

The production method according to the invention yields ninhydrin-type sorbents that have a surprisingly high capacity for binding nucleophilic waste solutes such as urea. Without wishing to be bound by theory, it is speculated that the more efficient conversion of precursor monomers into ninhydrin-type monomers contributes to this increased binding capacity. In preferred embodiments of this aspect, the invention provides a ninhydrin type sorbent according to the invention, wherein the sorbent has a urea binding capacity of more than 1.5 mmol urea per gram of sorbent. In more preferred embodiments of this aspect, the invention provides a ninhydrin type sorbent according to the invention, wherein the sorbent has a urea binding capacity of more than 1.6 mmol urea per gram of sorbent. In further preferred embodiments of this aspect, the invention provides a ninhydrin type sorbent according to the invention, wherein the sorbent has a urea binding capacity of more than 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.67, 1.68, 1.69, 1.70, 1.71, 1.72, 1.73, 1.74, 1.75, 1.76, 1.77, 1.78, 1.79, 1.80, 1.85, 1.90, 1.95, 2.00, 2.05, 2.10, 2.15, 2.20, 2.25, 2.30, 2.35, 2.40, 2.45, 2.50, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9 mmol urea per gram of sorbent; more preferably the sorbent has a urea binding capacity of more than 2.10, 2.15, 2.20, 2.25, 2.30, 2.35, 2.40, 2.45, 2.50, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9 mmol urea per gram of sorbent; even more preferably the sorbent has a urea binding capacity of more than 2.20, 2.25, 2.30, 2.35, 2.40, 2.45, 2.50, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9 mmol urea per gram of sorbent; most preferably the sorbent has a urea binding capacity of more than 2.40, 2.45, 2.50, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9 mmol urea per gram of sorbent, such as of more than 2.5 or of more than 2.6 mmol urea per gram of sorbent. Alternately, the sorbent has a urea binding capacity that is 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 times as high as that of a reference sorbent, wherein the reference sorbent is preferably the sorbent as described in example 2 of EP121275A1. In this aspect the invention also provides a ninhydrin type sorbent according to the invention, wherein the sorbent has a urea binding capacity of more than 2 mmol urea per gram of sorbent or of more than 2.1 mmol urea per gram of sorbent, which is particularly suitable for miniaturisation of an artificial kidney device or of a (hemo)dialysis device.

In this context, the urea binding capacity is preferably the maximum urea binding capacity, which is preferably the capacity that can be determined after incubation of a sorbent with an excess of urea in a solution (such as about 30 mM) at about 70° C. for about 24 hours. The amount of bound urea can be determined by directly analysing the amount of urea bound to the sorbent, or by analysing the difference between the amount of urea present in the solution before and after exposure to the sorbent, or by regenerating the sorbent by dissociating the bound urea, and subsequent determination of the amount of released urea. Urea concentration can be determined by any method known in the art, such as by elemental analysis as described in WO2004078797. Alternately, the amount of ammonia released by an urease enzyme can be used to indirectly quantify urea concentrations. Alternately, a PAB reagent solution containing about 4% (w:v) of 4-(dimethylamino)benzaldehyde and 4% (v:v) sulphuric acid in absolute ethanol can be used for UV-VIS analysis (422 nm) of the urea reaction adduct using a previously prepared calibration curve, as described in WO2016126596. Various kits for determining urea concentration are commercially available, and contain instructions for use.

In ninhydrin-type sorbents according to the invention at least 5%, 10%, 15%, 20%, 25%, 30%, 35%, 40%, 45%, 50%, 55%, 60%, 65%, 70%, 75%, 80%, 85%, 90%, 95%, or 100% of the polymerized monomers is a ninhydrin-type monomer. A preferred ninhydrin-type sorbent according to the invention is a ninhydrin type sorbent wherein at least 30%, 35%, 40%, 45%, 50%, 55%, 60%, 65%, 70%, 75%, 80%, 85%, 90%, 95%, or 100% of the polymerized monomers is a ninhydrin-type monomer, preferably at least 50%, more preferably at least 60%, even more preferably at least 70%, still more preferably at least 80%, and most preferably at least 90%. In further preferred ninhydrin-type sorbents according to the invention, at least 50% and at most 90% of the polymerized monomers is a ninhydrin-type monomer. In more preferred embodiments, 55% to 90% of the polymerized monomers is a ninhydrin-type monomer. In even more preferred embodiments, 70% to 90% of the polymerized monomers is a ninhydrin-type monomer. In most preferred embodiments, 70% to 80% of the polymerized monomers is a ninhydrin-type monomer. The amount of ninhydrin-type monomer is preferably reported as the amount of monomer of general formula (I) that was used during polymerization. Alternately, the amount of ninhydrin-type monomer can be assessed using conventional techniques known in the art, such as solid state NMR or IR spectroscopy, as exemplified in the examples.

In a particular embodiment of this aspect the invention provides a ninhydrin-type sorbents according to the invention wherein 100% of the polymerized monomers is a ninhydrin-type monomer. Such a polymer is particularly suitable for use outside of resins, such as in a pharmaceutical composition for oral administration.

In preferred embodiments, the ninhydrin-type sorbent according to the invention is obtainable by a production method according to the invention wherein the polymerization is suspension polymerisation. In preferred embodiments, the ninhydrin-type sorbent according to the invention is obtainable by a production method according to the invention wherein at most 50%, preferably at most 35%, more preferably at most 25%, even more preferably at most 20%, most preferably at most 10% cross-linking monomer is used.

Ninhydrin-type sorbents according to the invention are obtainable by a production method according to the invention, and can thus comprise comonomers and crosslinks as described for the method of the invention.

Method of Production

As described, the first aspect of the invention provides a method comprising the steps of
i) providing a monomer of general formula (I):

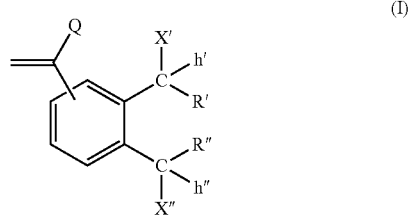

wherein:
Q is —H or —CH$_3$;
h' and h" are each independently absent or chosen from a halogen or —H;
X' and X" are each independently chosen from a halogen, —H, =O, =N—(CH$_2$)$_n$—H, —O—(CH$_2$)$_n$—H, —O—C(CH$_3$)$_3$, —O—CH(CH$_3$)$_2$, —(CH$_2$)$_n$—H, and —N(—[CH$_2$]$_n$—H)$_2$, wherein any —H may be optionally replaced by a halogen, wherein each instance of n is independently chosen from 0, 1, 2, 3, or 4, R' and R" are each independently chosen from a halogen, —H, —OH, —O—(CH$_2$)$_n$—H, —O—C(CH$_3$)$_3$, —O—CH(CH$_3$)$_2$, —N(—[CH$_2$]$_n$H)$_2$, and —(CH$_2$)$_n$—H, wherein any —H may be optionally replaced by a halogen, wherein each instance of n is independently chosen from 0, 1, 2, 3, or 4, or wherein R' and R" together form a bridging moiety selected from —CH$_2$—, =CH—, —C(=O)—, —C(—OH)$_2$—, —C(—OH)$_2$—C(—OH)$_2$—, —O—, —NH—, and —C(h''')(X''')—, wherein
h''' is independently chosen as defined for h' or is —NH—C(=O)—NH$_2$;
X''' is independently chosen as defined for X'; or wherein X''' is —OH and h''' and one of h' or h" together form a bridging moiety —NH—C(=O)—NH—;
ii) polymerizing the provided monomer to obtain a polymer; and
iii) converting polymerized monomers of general formula (I) that are not ninhydrin-type monomers into ninhydrin-type monomers.

Step i)—Provision of a Monomer

In step i) a monomer is provided. The monomer can be synthesized using conventional techniques such as exemplified in the examples, or it can be procured from a commercial source. A monomer can already have a ninhydrin-type moiety, or it can be converted into a monomer having a ninhydrin-type monomer via subsequent reaction steps. Such a monomer that requires conversion is referred to herein as a precursor monomer. Preferably, a precursor monomer can be converted into a monomer comprising a ninhydrin-type moiety in 1, 2, 3, or 4 reaction steps, more preferably in 1, 2, or 3 reaction steps, even more preferably in 1 or 2 reactions steps, most preferably in 1 reaction step. Because monomers of general formula (I) encompass both monomers with a ninhydrin-type moiety and precursor monomers, it is preferred that a monomer of general formula (I) can be converted into a monomer comprising a ninhydrin-type moiety in 0, 1, 2, 3, or 4 reaction steps, more preferably in 0, 1, 2, or 3 reaction steps, even more preferably in 0, 1, or 2 reaction steps, most preferably in 0 or 1 reaction steps. Reactions and reaction steps will be defined later herein, in the section detailing step iii).

The monomer features a handle for polymerization which is a vinyl (when Q is —H) or methylvinyl (when Q is —CH$_3$) moiety. Vinyl is also called ethenyl, and methylvinyl is also called isopropenyl, which should be interpreted as propenyl linked at its central carbon atom. This moiety comprising Q is linked to the ring that will be, after the conversion of step iii), the aromatic part of the ninhydrin-type moiety. It can be in position 4, 5, 6, or 7 of the ninhydrin-type moiety, which due to the symmetry of general formula (I) means that it can be at position 4 or 5, which is the same as being at position 6 or 7, depending on other substituents. When a less hydrophobic or more flexible ninhydrin-type sorbent according to the invention is desired, it is preferred to use a monomer of general formula (I) wherein Q is —H, because this leads to a more flexible and less aliphatically bulky backbone of the resultant polymer.

The monomer further features two —CXRh moieties, which allow the monomer to be readily and efficiently converted into a ninhydrin-type moiety in step iii), or which together already form a ninhydrin-type moiety, optionally bound to urea. A skilled person understands the valency of atoms, and understands that monomers of general formula (I) comply with such valency, such that for example when either of X or R is bivalent, such as =O, h is absent. The two R groups often form a bridging moiety, completing a five- or six-membered ring. In preferred embodiments, R' and R" together form a bridging moiety selected from —CH$_2$—, =CH—, —C(=O)—, —C(—OH)$_2$—, —C(—OH)$_2$—C(—OH)$_2$—, —O—, —NH—, or —C(h''')(X''')—, wherein h''' and X''' are as defined later herein.

In preferred monomers of general formula (I),

Q is —H;

h' and h" are each independently absent or —H;

X' and X" are each independently chosen from —H, =O, —O—(CH$_2$)$_n$—H, —O—C(CH$_3$)$_3$, —O—CH(CH$_3$)$_2$, and —(CH$_2$)$_n$—H, wherein any —H may be optionally replaced by a halogen, wherein each instance of n is independently chosen from 0, 1, 2, 3, or 4, R' and R" are each independently chosen from —H, —OH, —O—(CH$_2$)$_n$—H, —O—C(CH$_3$)$_3$, —O—CH(CH$_3$)$_2$, and —(CH$_2$)$_n$—H, wherein any —H may be optionally replaced by a halogen, wherein each instance of n is independently chosen from 0, 1, 2, 3, or 4, or wherein R' and R" together form a bridging moiety selected from —CH$_2$—, =CH—, —C(=O)—, —C(—OH)$_2$—, —O—, and —C(h''')(X''')—, wherein h''' is independently chosen as defined for h';

X''' is independently chosen as defined for X'; or wherein X''' is —OH and h''' and one of h' or h" together form a bridging moiety —NH—C(=O)—NH—.

In more preferred monomers of general formula (I),

Q is —H;

h' and h" are each independently absent or —H;

X' and X" are each independently chosen from —H and =O.

R' and R" are each independently chosen from —OH, —O—(CH$_2$)$_n$—H, wherein any —H may be optionally replaced by a halogen, wherein each instance of n is independently chosen from 0, 1, 2, 3, or 4, or wherein R' and R" together form a bridging moiety selected from —CH$_2$—, =CH—, —C(=O)—, —C(—OH)$_2$—, —O—, and —C(h''')(X''')—, wherein h''' is independently chosen as defined for h';

X''' is independently chosen as defined for X'; or wherein X''' is —OH and h''' and one of h' or h" together form a bridging moiety —NH—C(=O)—NH—.

Monomers of general formula (I) can be of general formula (Ii), of general formula (Ip), or of general formula (In) as shown below:

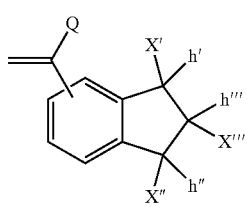

(Ii)

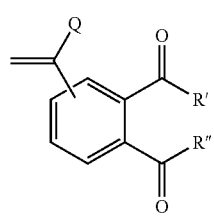

(Ip)

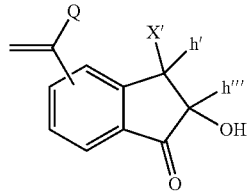

(In)

In preferred embodiments, a monomer of general formula (I) is of general formula (Ii), wherein Q is —H or —CH$_3$ and wherein h' and h" and h''' are each independently absent or chosen from a halogen or —H, and wherein X' and X" and X''' are each independently chosen from a halogen, —H, =O, —N—(CH$_2$)$_n$—H, —O—(CH$_2$)$_n$—H, —O—C(CH$_3$)$_3$, —O—CH(CH$_3$)$_2$, —(CH$_2$)$_n$—H, and —N(—[CH$_2$]$_n$—H)$_2$, wherein any —H may be optionally replaced by a halogen, wherein each instance of n is independently chosen from 0, 1, 2, 3, or 4, or wherein h" forms a bond with either h' or h'''. Preferably, X' and X" and X''' are each independently chosen from —H and =O, and h' and h" and h''' are each independently —H or absent, or wherein h" forms a bond with either h' or h'''. For a monomer of general formula (Ii), the moiety comprising Q can be at position 4, 5, 6, or 7 of the phenyl ring, preferably it is at position 5 or 6, most preferably at position 6. A monomer of general formula (Ii) wherein any one of X', X", or X''' is =O is referred to herein as an indanone-type monomer.

In preferred embodiments, a monomer of general formula (I) is of general formula (Ip), wherein Q is —H or —CH$_3$, and wherein R' and R" are each independently chosen from a halogen, —H, —OH, —O—(CH$_2$)$_n$—H, —O—C(CH$_3$)$_3$, —O—CH(CH$_3$)$_2$, —N(—[CH$_2$]$_n$H)$_2$, and —(CH2)$_n$—H, wherein any —H may be optionally replaced by a halogen, wherein each instance of n is independently chosen from 0, 1, 2, 3, or 4, or wherein R' and R" together form a bridging moiety —O—. Preferably, R' nd R" are each independently chosen from —H, —OH, —OCH$_3$, and —O—CH$_2$—CH$_3$, or together form a bridging moiety —O—. For a monomer of general formula (Ip), the moiety comprising Q can be at position 4, 5, 6, or 7 of the phenyl ring, preferably it is at position 5 or 6, most preferably at position 6.

In preferred embodiments, a monomer of general formula (I) is of general formula (In), wherein Q is —H or —CH$_3$, and wherein either h''' is —OH, X' is =O, and h' is absent, or h''' is —NH—C(=O)—NH$_2$, is =O, and h' is absent, or X' is —OH, and h' and h''' together form a bridging moiety —NH—C(=O)—NH—. For a monomer of general formula (In), the moiety comprising Q can be at position 4, 5, 6, or 7 of the phenyl ring, preferably it is at position 5 or 6, most preferably at position 6.

In preferred embodiments, a monomer of general formula (I) is of general formula (In) or of general formula (Ii), wherein Q, h', h", X', X", and X''' are as described above.

Suitable monomers of general formula (I) are shown below.

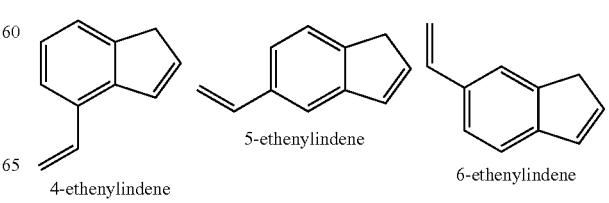

4-ethenylindene  5-ethenylindene  6-ethenylindene

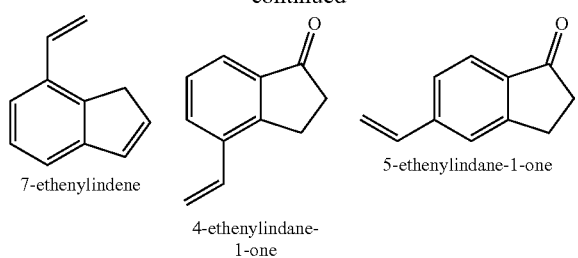
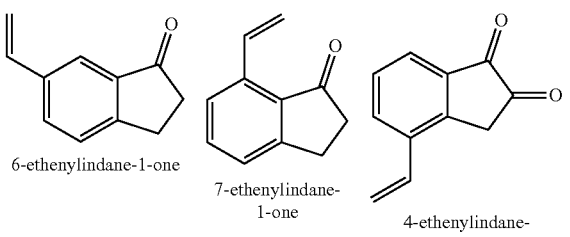
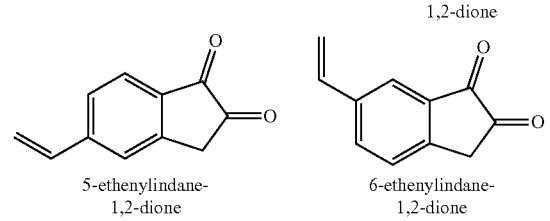
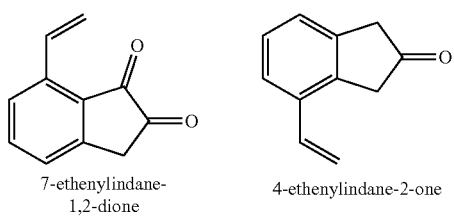
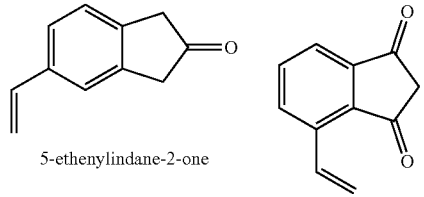
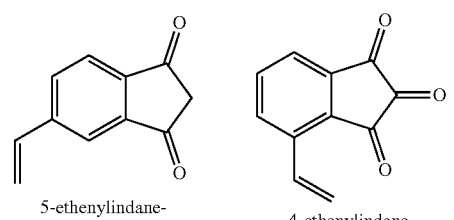
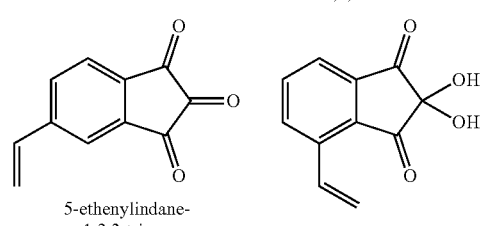
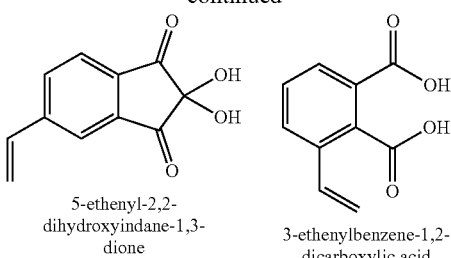
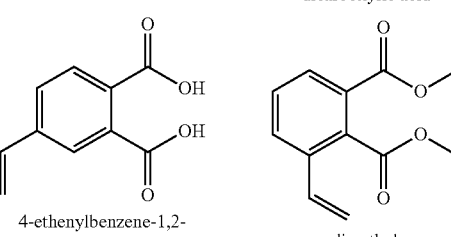
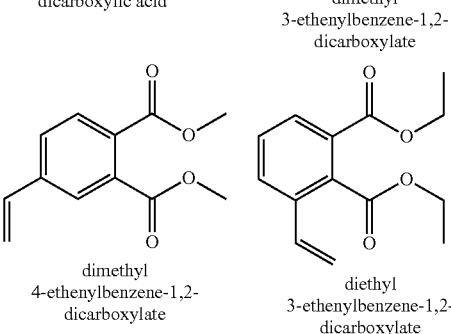
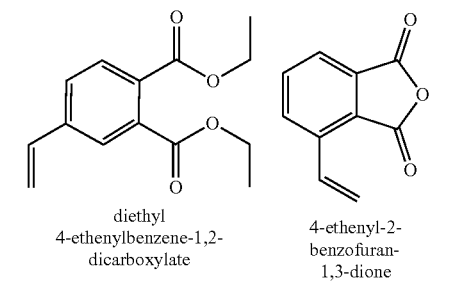
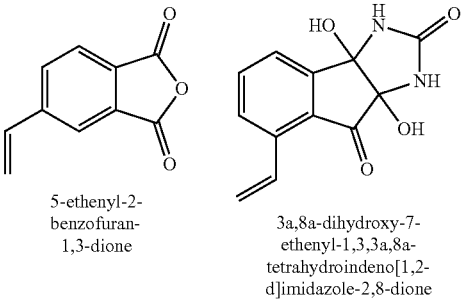
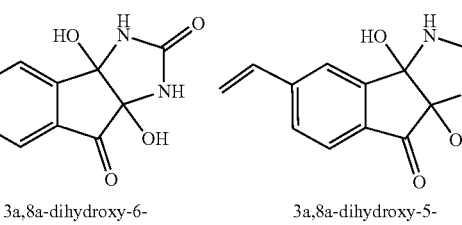

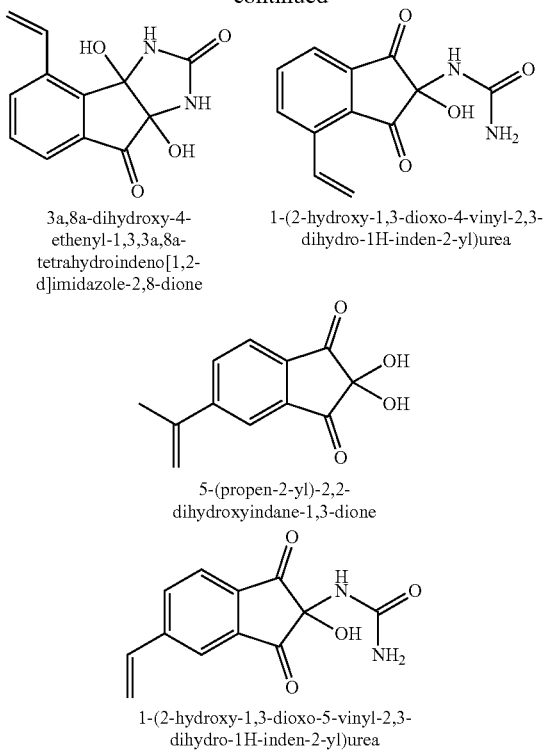

3a,8a-dihydroxy-4-ethenyl-1,3,3a,8a-tetrahydroindeno[1,2-d]imidazole-2,8-dione 1-(2-hydroxy-1,3-dioxo-4-vinyl-2,3-dihydro-1H-inden-2-yl)urea 5-(propen-2-yl)-2,2-dihydroxyindane-1,3-dione 1-(2-hydroxy-1,3-dioxo-5-vinyl-2,3-dihydro-1H-inden-2-yl)urea In preferred embodiments of this aspect, the invention provides the production method according to the invention, wherein the monomer of general formula (I) is selected from the group consisting of: 4-ethenylindene, 5-ethenylindene, 6-ethenylindene, 7-ethenylindene, 4-ethenylindane-1-one, 5-ethenylindane-1-one, 6-ethenylindane-1-one, 7-ethenylindane-1-one, 4-ethenylindane-1,2-dione, 5-ethenylindane-1,2-dione, 6-ethenylindane-1,2-dione, 7-ethenylindane-1,2-dione, 4-ethenylindane-2-one, 5-ethenylindane-2-one, 4-ethenylindane-1,3-dione, 5-ethenylindane-1,3-dione, 4-ethenylindane-1,2,3-trione, 5-ethenylindane-1,2,3-trione, 4-ethenyl-2,2-dihydroxyindane-1,3-dione, 5-ethenyl-2,2-dihydroxyindane-1,3-dione, 3-ethenylbenzene-1,2-dicarboxylic acid, 4-ethenylbenzene-1,2-dicarboxylic acid, dimethyl 3-ethenylbenzene-1,2-dicarboxylate, dimethyl 4-ethenylbenzene-1,2-dicarboxylate, diethyl 3-ethenylbenzene-1,2-dicarboxylate, diethyl 4-ethenylbenzene-1,2-dicarboxylate, 4-ethenyl-2-benzofuran-1,3-dione, 5-ethenyl-2-benzofuran-1,3-dione, 3a,8a-dihydroxy-7-ethenyl-1,3,3a,8a-tetrahydroindeno[1,2-d]imidazole-2,8-dione, 3a,8a-dihydroxy-6-ethenyl-1,3,3a,8a-tetrahydroindeno[1,2-d]imidazole-2,8-dione, 3a,8a-dihydroxy-5-ethenyl-1,3,3a,8a-tetrahydroindeno[1,2-d]imidazole-2,8-dione, and 3a,8a-dihydroxy-4-ethenyl-1,3,3a,8a-tetrahydroindeno[1,2-d]imidazole-2,8-dione, optionally selected from isopropenyl analogues thereof.

In more preferred embodiments, the invention provides the production method according to the invention, wherein the monomer of general formula (I) is selected from the group consisting of: 5-ethenylindene, 6-ethenylindene, 5-ethenylindane-1-one, 6-ethenylindane-1-one, 5-ethenylindane-1,3-dione, 5-ethenylindane-1,2,3-trione, 5-ethenyl-2,2-dihydroxyindane-1,3-dione, 4-ethenylbenzene-1,2-dicarboxylic acid, dimethyl 4-ethenylbenzene-1,2-dicarboxylate, diethyl 4-ethenylbenzene-1,2-dicarboxylate, 3a,8a-dihydroxy-6-ethenyl-1,3,3a,8a-tetrahydroindeno[1,2-d]imidazole-2,8-dione, and 3a,8a-dihydroxy-5-ethenyl-1,3,3a,8a-tetrahydroindeno[1,2-d]imidazole-2,8-dione, or optionally selected from isopropenyl analogies thereof.

In further preferred embodiments, the invention provides the production method according to the invention, wherein the monomer of general formula (I) is selected from the group consisting of: 4-ethenylindene, 5-ethenylindene, 6-ethenylindene, 7-ethenylindene, 4-ethenylindane-1-one, 5-ethenylindane-1-one, 6-ethenylindane-1-one, 7-ethenylindane-1-one, 4-ethenylindane-1,2-dione, 5-ethenylindane-1,2-dione, 6-ethenylindane-1,2-dione, 7-ethenylindane-1,2-dione, 4-ethenylindane-2-one, 5-ethenylindane-2-one, 4-ethenylindane-1,3-dione, 5-ethenylindane-1,3-dione, 4-ethenylindane-1,2,3-trione, and 5-ethenylindane-1,2,3-trione, optionally selected from isopropenyl analogues thereof. Such monomers are of general formula (Ii).

In further preferred embodiments, the invention provides the production method according to the invention, wherein the monomer of general formula (I) is selected from the group consisting of: 4-ethenyl-2,2-dihydroxyindane-1,3-dione, 5-ethenyl-2,2-dihydroxyindane-1,3-dione, 3a,8a-dihydroxy-7-ethenyl-1,3,3a,8a-tetrahydroindeno[1,2-d]imidazole-2,8-dione, 3a,8a-dihydroxy-6-ethenyl-1,3,3a,8a-tetrahydroindeno[1,2-d]imidazole-2,8-dione, 3a,8a-dihydroxy-5-ethenyl-1,3,3a,8a-tetrahydroindeno[1,2-d]imidazole-2,8-dione, and 3a,8a-dihydroxy-4-ethenyl-1,3,3a,8a-tetrahydroindeno[1,2-d]imidazole-2,8-dione, optionally selected from isopropenyl analogues thereof. Such monomers are of general formula (Ip).

In further preferred embodiments, the invention provides the production method according to the invention, wherein the monomer of general formula (I) is selected from the group consisting of: 3-ethenylbenzene-1,2-dicarboxylic acid, 4-ethenylbenzene-1,2-dicarboxylic acid, dimethyl 3-ethenylbenzene-1,2-dicarboxylate, dimethyl 4-ethenylbenzene-1,2-dicarboxylate, diethyl 3-ethenylbenzene-1,2-dicarboxylate, diethyl 4-ethenylbenzene-1,2-dicarboxylate, 4-ethenyl-2-benzofuran-1,3-dione, and 5-ethenyl-2-benzofuran-1,3-dione, optionally selected from isopropenyl analogues thereof. Such monomers are of general formula (In).

It is particularly envisaged that provision of a monomer of general formula (I) may entail the provision of a mixture of monomers of general formula (I). Preferably, the compounds present in such a mixture differ only in their attachment position of the moiety comprising Q. As such:

when any one of 4-ethenylindene, 5-ethenylindene, 6-ethenylindene, or 7-ethenylindene is provided, preferably a mixture of each of these monomers can also be provided;

when any one of 4-ethenylindane-1-one, 5-ethenylindane-1-one, 6-ethenylindane-1-one, or 7-ethenylindane-1-one is provided, preferably a mixture of each of these monomers can also be provided;

when any one of 4-ethenylindane-1,2-dione, 5-ethenylindane-1,2-dione, 6-ethenylindane-1,2-dione, or 7-ethenylindane-1,2-dione is provided, preferably a mixture of each of these monomers can also be provided;

when 4-ethenylindane-2-one or 5-ethenylindane-2-one is provided, preferably also both of these monomers can be provided in a mixture;

when 4-ethenylindane-1,3-dione or 5-ethenylindane-1,3-dione is provided, preferably also both of these monomers can be provided in a mixture;

when 4-ethenylindane-1,2,3-trione or 5-ethenylindane-1,2,3-trione is provide, preferably also both of these monomers can be provided in a mixture when 4-ethenyl-2,2-dihydroxyindane-1,3-dione or 5-ethenyl-2,2-dihydroxyindane-1,3-dione is provided, preferably also both of these monomers can be provided in a mixture;

when 3-ethenylbenzene-1,2-dicarboxylic acid or 4-ethenylbenzene-1,2-dicarboxylic acid is provided, preferably also both of these monomers can be provided in a mixture;

when dimethyl 3-ethenylbenzene-1,2-dicarboxylate or dimethyl 4-ethenylbenzene-1,2-dicarboxylate is provided, preferably also both of these monomers can be provided in a mixture;

when diethyl 3-ethenylbenzene-1,2-dicarboxylate or diethyl 4-ethenylbenzene-1,2-dicarboxylate is provided, preferably also both of these monomers can be provided in a mixture;

when 4-ethenyl-2-benzofuran-1,3-dione or 5-ethenyl-2-benzofuran-1,3-dione is provided, preferably also both of these monomers can be provided in a mixture;

when any one of 3a,8a-dihydroxy-7-ethenyl-1,3,3a,8a-tetrahydroindeno[1,2-d]imidazole-2,8-dione, 3a,8a-dihydroxy-6-ethenyl-1,3,3a,8a-tetrahydroindeno[1,2-d]imidazole-2,8-dione, 3a,8a-dihydroxy-5-ethenyl-1,3,3a,8a-tetrahydroindeno[1,2-d]imidazole-2,8-dione, or 3a,8a-dihydroxy-4-ethenyl-1,3,3a,8a-tetrahydroindeno[1,2-d]imidazole-2,8-dione is provided, preferably a mixture of each of these monomers can also be provided;

wherein the same is applicable for isopropenyl analogues of any of the above. Due to the synthetic accessibility of the various monomers, it is unlikely that isopropenyl and ethenyl analogues would be provided as a mixture, as these require different reactants.

Step ii)—Polymerization

In step ii), the monomers that were provided in step i) are polymerized to obtain a polymer. A polymer is a substance composed of macromolecules, wherein a macromolecule is a molecule of high relative molecular mass, the structure of which essentially comprises the multiple repetition of units derived, actually or conceptually, from molecules of low relative molecular mass. A polymer can be a single chain composed of one type of monomer, and a polymer can also be a large crosslinked network composed of many different monomers. As is known in the art, polymerization is the process of forming a polymer out of monomers.

Polymerization takes place via the moiety comprising Q, and can be via any method known in the art (see for instance S. M. Ashraf "A Laboratory Manual of Polymers" I. K. International Pvt Ltd, 8 Dec. 2008). Suitable methods for polymerizing vinyl or methylvinyl type monomers such as those of general formula (I) are radical polymerization, bond-insertion polymerization, and ionic polymerization. Examples of ionic polymerization are anionic polymerization and cationic polymerization. An example of bond-insertion polymerization is Ziegler-Natta polymerization. Examples of radical polymerization are free radical polymerization, atom transfer radical polymerization (ATRP), and radical addition fragmentation chain transfer polymerization (RAFT). Suspension polymerization using immiscible solvents is a preferred method because it can lead to a granulated sorbent. A skilled person knows how to perform such polymerizations.

Solvents can also be present as inert solvents; these are preferably dissolving inert solvents. Depending on the context an inert solvent can also be a mixture of inert solvents. The inert solvent can influence the porosity of the produced sorbent; accordingly the inert solvent can also be referred to as a porogen. A more polar inert solvent can lead to an increased porosity; a less polar inert solvent can lead to a more dense sorbent. A more polar inert solvent can lead to decreased mechanical stability of the resulting sorbent; a less polar inert solvent can lead to more mechanical stability in the resulting sorbent. Accordingly, the inert solvent preferably has a polarity that combines desirable porosity with desirable mechanical stability.

Suitable inert solvents are known in the art; examples are pentane, hexane, heptane, cyclohexane, benzene, toluene, xylene, nitrobenzene, nitromethane, furan, tetrahydrofuran, 1,4-dioxane, isoparaffin aliphatic hydrocarbons such as ShellSolTD (CAS 64761-65-7; Shell Chemicals product code for Europe: Q7411) or ShellSolT (CAS 64761-65-7; Shell Chemicals product code for Europe: Q7412), or mixtures thereof. Preferred inert solvents are pentane, hexane, heptane, cyclohexane, benzene, toluene, xylene, nitrobenzene, nitromethane, furan, tetrahydrofuran, 1,4-dioxane, ShellSolTD, ShellSolT, or mixtures thereof. More preferred inert solvents are pentane, hexane, heptane, cyclohexane, benzene, toluene, xylene, nitrobenzene, nitromethane, ShellSolTD, ShellSolT, or mixtures thereof. Even more preferred inert solvents are heptane, toluene, nitrobenzene, ShellSolTD, optionally nitromethane, or mixtures thereof; toluene is most preferred.

Mixtures of inert solvents are convenient when a specific polarity is desired, for example when more porosity is desired, an inert solvent with higher polarity should be selected. Examples of suitable mixtures of inert solvents are toluene:nitromethane, toluene:nitrobenzene; toluene:heptane; and toluene:ShellSolTD. Preferred mixtures of inert solvents are toluene:nitrobenzene (1:1); toluene:heptane (1:4); toluene:heptane (1:1); and toluene:ShellSolTD (1:4). More preferred mixtures of inert solvents are toluene:nitrobenzene (1:1); toluene:heptane (1:4); and toluene:heptane (1:1).

In preferred embodiments the inert solvent or mixture of inert solvents is not more polar than nitrobenzene and/or not less polar than heptane. In more preferred embodiments the inert solvent or mixture of inert solvents is not more polar than nitrobenzene and not less polar than heptane. In even more preferred embodiments the inert solvent or mixture of inert solvents is not more polar than nitrobenzene and/or not less polar than heptane:toluene (4:1). In most preferred embodiments the inert solvent or mixture of inert solvents is not more polar than nitrobenzene and/or not less polar than heptane:toluene (4:1). Polarity preferably refers to the average polarity of the inert solvent or of the average polarity of the mixture of inert solvents; it can be determined using any method known in the art, for example as described in Katritzky et al., Chem. Rev. (2004) DOI: 10.1021/cr020750m.

For productions methods according to the invention, it is preferred that step ii) entails polymerizing the provided monomer to obtain a polymer using radical polymerization, more preferably free radical polymerization. This is because the process of free radical polymerization is readily implemented and does not require complex setups or conditions. Suitable initiators for free radical polymerization are azobisisobutyronitrile (AIBN), benzoyl peroxide, benzoyl peroxide blend with dicyclohexyl phthalate, 1,1'-azobis(cyclohexanecarbonitrile) (ABCN), di-tert-butyl peroxide, acetone peroxide, methyl ethyl ketone peroxide, and peroxydisulfate salts such as sodium persulfate or potassium persulfate or ammonium persulfate. For aqueous systems, AIBN and/or peroxydisulfate salts, particularly potassium persulfate, are preferred. For suspension polymerization preferred initiators are benzoyl peroxide and/or benzoyl peroxide blend with dicyclohexyl phthalate.

During polymerization, a comonomer that is not of general formula (I) can also be present. Comonomers are further monomers that undergo the polymerization of step ii) in the same mixture as the monomers provided in step i), and comonomers become covalently incorporated in the resulting polymer. Such a resulting polymer is often referred to as a copolymer, but for sake of clarity this document will only refer to polymers as such, where the context will make it clear whether a copolymer could also be referenced. In the context of this invention, two classes of comonomers are particularly relevant: hydrophilic comonomers and crosslinking comonomers.

In preferred embodiments, the invention provides a production method according to the invention, wherein a comonomer is provided along with the monomer of general formula (I), wherein the comonomer is preferably selected from the group consisting of styrene, isopropenylbenzene, divinylbenzene, vinylbenzenesulfonic acid, acrylic acid, methacrylic acid, methyl acrylate, methyl methacrylate, ethyl acrylate, ethyl methacrylate, acrylonitrile, 2-hydroxyethyl 2-methylprop-2-enoate (HEMA), 2-hydroxypropyl 2-methylprop-2-enotate, 2-hydroxyethyl prop-2-enoate, 2-hydroxypropyl prop-2-enotate, N-(2-hydroxyethyl)methacrylamide, N-(2-hydroxypropyl)methacrylamide (HPMA), N-(2-hydroxyethyl)acrylamide, N-(2-hydroxypropyl)acrylamide, a telechelic N,N'-alkylenebisacrylamide such as N,N'-methylenebisacrylamide (NMAA), N-isopropylacrylamide (NIPAm), divinyl sulfone, and butadiene. In more preferred embodiments, the invention provides a production method according to the invention, wherein a comonomer is provided along with the monomer of general formula (I), wherein the comonomer is selected from the group consisting of divinylbenzene, vinylbenzenesulfonic acid, acrylic acid, and 2-hydroxyethyl 2-methylprop-2-enoate (HEMA). Even more preferably, the comonomer is selected from the group consisting of divinylbenzene and vinylbenzenesulfonic acid. Most preferably, both divinylbenzene and vinylbenzenesulfonic acid are provided along with the monomer of general formula (I).

In the context of this invention, divinylbenzene can be either 1,2-diethenylbenzene, 1,3-diethenylbenzene, or 1,4-diethenylbenzene, or mixtures thereof. 1,4-diethenylbenzene or mixtures comprising 1,4-diethenylbenzene are preferred because these provide a more spacious crosslink, which improves the solvent-permeability of the resulting polymer.

In the context of this invention, vinylbenzenesulfonic acid can be either 2-vinylbenzenesulfonic acid, 3-vinylbenzenesulfonic acid, or 4-vinylbenzenesulfonic acid, or mixtures thereof. 4-vinylbenzenesulfonic acid is preferred because of its desirable polymerization kinetics. Vinylbenzenesulfonic acid can be provided as a salt, such as sodium vinylbenzenesulfonic acid, or calcium (vinylbenzenesulfonic acid)$_2$. The provision of salts of vinylbenzenesulfonic acid can improve the solubility of this comonomer and is particularly suitable when polymerization takes place in aqueous or otherwise highly polar media.

For crosslinked sorbents, it is preferred that at least one crosslinking comonomer is provided along with the monomer of general formula (I). A crosslinking comonomer generally has more than one reactive moiety that can participate in the polymerization reaction. Preferably, such a crosslinking comonomer is selected from the group consisting of: divinylbenzene, a telechelic N,N'-alkylenebisacrylamide such as N,N'-methylenebisacrylamide (NMAA), divinyl sulfone, and butadiene, preferably divinylbenzene is provided along with the monomer of general formula (I).

Alternately, the polymer can be crosslinked after the polymerization of step ii), for example by reacting polymer chains with one another, possibly via side chains of comonomers. As such, in preferred embodiments the invention provides a production method according to the invention, wherein the polymer is crosslinked after polymerization or during polymerization. Preferably, the polymer is crosslinked during polymerization, more preferably using a crosslinking comonomer.

In the context of this invention, the amount of crosslinking is defined as the amount of crosslinking comonomers that was present in the polymerization mixture during step ii). A larger amount of crosslinking results in more dense sorbents; a smaller amount of crosslinking results in more porous or more macroporous sorbents. Preferably, at most 10% crosslinking comonomer is used. More preferably, at most 5% crosslinking comonomer is used. Even more preferred, for crosslinked sorbents, from 0.1% to 5% crosslinking comonomer is used, more preferably 0.2% to 4% crosslinking comonomer is used, even more preferably 0.4% to 4% crosslinking comonomer is used, most preferably 0.8% to 3% crosslinking comonomer is used, such as about 1% to about 2%, or about 2%.

In preferred embodiments, less than 80% crosslinking comonomer is used. In more preferred embodiments, less than 67% crosslinking comonomer is used. In highly preferred embodiments, less than 50% crosslinking comonomer is used. In most preferred embodiments, less than 10% crosslinking comonomer is used. Accordingly, in preferred embodiments 1% to 10% crosslinking comonomer is used; in more preferred embodiments 2% to 10% crosslinking comonomer is used; in even more preferred embodiments 2% to 8% crosslinking comonomer is used; in still more preferred embodiments 2% to 7% crosslinking comonomer is used; in most preferred embodiments 3% to 6% crosslinking comonomer is used.

A sorbent comprising a hydrophilic comonomer is referred to herein as a hydrophilic sorbent. A hydrophilic comonomer enables aqueous solvents to more easily permeate the sorbent, so that nucleophilic waste solutes can similarly more easily permeate the sorbent. This allows the interior of the sorbent to also participate in the binding of nucleophilic waste solutes. There is a balance, because hydrophilic comonomers generally cannot bind nucleophilic waste solutes in the way that ninhydrin-type moieties can. Thus, the increase in hydrophilic comonomer content makes ninhydrin-type moieties more effective, but reduces their number.

For hydrophilic sorbents, it is preferred that at least one hydrophilic comonomer is provided along with the monomer of general formula (I). Preferably, such a hydrophilic comonomer is selected from the group consisting of: vinylbenzenesulfonic acid, acrylic acid, methacrylic acid, methyl acrylate, methyl methacrylate, ethyl acrylate, ethyl methacrylate, 2-hydroxyethyl 2-methylprop-2-enoate (HEMA), 2-hydroxypropyl 2-methylprop-2-enotate, 2-hydroxyethyl prop-2-enoate, 2-hydroxypropyl prop-2-enotate, N-(2-hydroxyethyl)methacrylamide, N-(2-hydroxypropyl)methacrylamide (HPMA), N-(2-hydroxyethyl)acrylamide, N-(2-hydroxypropyl)acrylamide, and N-isopropylacrylamide (NIPAm), more preferably from the group consisting of: vinylbenzenesulfonic acid, acrylic acid, methacrylic acid, 2-hydroxyethyl 2-methylprop-2-enoate (HEMA), 2-hydroxypropyl 2-methylprop-2-enotate, 2-hydroxyethyl prop-2-enoate, 2-hydroxypropyl prop-2-enotate, N-(2-hydroxyethyl)methacrylamide, N-(2-hydroxypropyl)methacrylamide (HPMA), N-(2-hydroxyethyl)acrylamide, and N-(2-hydroxypropyl)acrylamide, preferably vinylbenzenesulfonic acid is provided along with the monomer of general formula (I). A skilled person will understand that some comonomers such as methyl methacrylate can easily be postmodified to become hydrophilic through hydrolysis of their ester. Preferably, at most 60% hydrophilic comonomer is used. More preferably, at most 50% hydrophilic comonomer is used. Even more preferred, for hydrophilic sorbents, from 0% to 50% hydrophilic comonomer is used, more preferably 0% to 40% hydrophilic comonomer is used, even more preferably 5% to 40% hydrophilic comonomer is used, more preferably still 10% to 35% hydrophilic comonomer is used, even more preferably still 15% to 35% hydrophilic comonomer is used, most preferably 20% to 30% hydrophilic comonomer is used, such as about 25%.

Step iii)—Conversion of Precursor Monomers

The polymer obtained in step ii) contains monomers of general formula (I), and these monomers can be precursor monomers that are not already ninhydrin-type monomers. In step iii) the precursor monomers comprised in the polymer obtained in step ii) are converted into ninhydrin-type monomers by performing a conversion reaction. A conversion reaction can comprise 1, 2, or 3 steps. In preferred embodiments, the invention provides the production method according to the invention, wherein step iii) comprises converting polymerized monomers of general formula (I) that are not ninhydrin-type monomers into ninhydrin-type monomers using 1, 2, or 3 reaction steps, preferably using 1 or 2 reaction steps, more preferably using 1 reaction step. When a monomer of general formula (I) already comprises a ninhydrin-type moiety, step iii) is effectively absent if no other monomers of general formula (I) are present.

Methods for converting molecules such as those of general formula (I) are known in the art, and a skilled person can select which reactions are suitable for converting any particular monomer of general formula (I) into a ninhydrin-type monomer. Conversion reactions depend on which monomer of general formula (I) is to be converted. Accordingly, in preferred embodiments the invention provides a production method according to the invention, wherein in step iii) a conversion reaction is used comprising a step selected from the group consisting of:

a) oxidation, preferably using an oxide such as $SeO_2$;
b) halogenation, preferably using $Br_2$, $Cl_2$, or $I_2$;
c) alkylation, preferably using dimethyl sulfoxide (DMSO) or ethyl acetoacetate, and optionally a hydrohalic acid such as HBr, HI, or HCl, preferably using DMSO and a hydrohalic acid such as HCl;
d) fragmentation, preferably by heating to about 80° C.; and
e) hydrolysis, preferably by heating to about 80° C. in an aqueous environment.

Preferred oxidation methods are the Swern oxidation, which uses DMSO and oxalyl chloride and a base, for example a trialkylamine such as trimethylamine; Dess-Martin oxidation, for example using Dess-Martin periodinane; Corey-Kim oxidation, for example using N-halosuccinimide such as N-chlorosuccinimide, and dimethyl sulfide, and a base, for example a trialkylamine such as trimethylamine; Oppenauer oxidation, for example using aluminium isopropoxide; Kornblum oxidation, for example using DMSO and oxalyl chloride and a base, for example a trialkylamine such as trimethylamine, or which omits the base when it follows a halogenation; or direct oxidation using oxides such as $SeO_2$, $OsO_4$, or $MnO_2$. A very suitable and therefore preferred oxidation method is microwave-assisted direct oxidation using oxides such as $SeO_2$, $OsO_4$, or $MnO_2$, as described by Marminon et al., (2015, DOI: 10.1016/j.tetlet.2015.02.086). Another highly preferred oxidation method is Kornblum oxidation following halogenation, using dimethyl sulfoxide (DMSO) or ethyl acetoacetate, and a hydrohalic acid such as HBr, HI, or HCl, preferably using DMSO and a hydrohalic acid such as HCl.

Halogenation can be performed using methods known in the art. Preferred methods use $Br_2$, $Cl_2$, or $I_2$ or N-halosuccinimides such as N-bromosuccinimide, N-chlorosuccinimide, or N-iodosuccinimide. In preferred embodiments, halogenation is done using $Br_2$, $Cl_2$, or $I_2$. In other preferred embodiments, halogenation is done using N-halosuccinimides such as N-bromosuccinimide, N-chlorosuccinimide, or N-iodosuccinimide.

More preferably, in step iii) a conversion reaction is used comprising a step selected from the group consisting of:

a) oxidation, preferably using an oxide such as $SeO_2$ or using dimethyl sulfoxide (DMSO) and hydrohalic acid, more preferably using DMSO and a hydrohalic acid such as HCl;
b) alkylation, preferably using dimethyl sulfoxide (DMSO) or ethyl acetoacetate, and optionally a hydrohalic acid such as HBr, HI, or HCl, preferably using DMSO and a hydrohalic acid such as HCl;
c) fragmentation, preferably by heating to about 80° C. or by incubation with an aqueous solution of at least 6M, preferably 12M hydrohalic acid, preferably HCl;
d) oxidation, preferably using an oxide such as $SeO_2$, followed by oxidation using dimethyl sulfoxide (DMSO) and hydrohalic acid, more preferably using DMSO and a hydrohalic acid such as HCl; and
e) hydrolysis, preferably by heating to about 80° C. in an aqueous environment.

Most preferably, in step iii) a conversion reaction is used consisting of a conversion reaction selected from the group consisting of:

a) alkylation, preferably using dimethyl sulfoxide (DMSO) or ethyl acetoacetate, and optionally a hydrohalic acid such as HBr, HI, or HCl, preferably using DMSO and a hydrohalic acid such as HCl, followed by hydrolysis, preferably by heating to about 80° C. in an aqueous environment;
b) oxidation, preferably using dimethyl sulfoxide (DMSO) or ethyl acetoacetate, and optionally a hydrohalic acid such as HBr, HI, or HCl, preferably using DMSO and a hydrohalic acid such as HCl, followed by hydrolysis, preferably by heating to about 80° C. in an aqueous environment;
c) oxidation, preferably using an oxide such as $SeO_2$, followed by oxidation, preferably using dimethyl sulfoxide (DMSO) or ethyl acetoacetate, and optionally a hydrohalic acid such as HBr, HI, or HCl, preferably using DMSO and a hydrohalic acid such as HCl, followed by hydrolysis, preferably by heating to about 80° C. in an aqueous environment
d) fragmentation, preferably by incubation with an aqueous solution of at least 6M, preferably 12M hydrohalic acid, preferably HCl.

The skilled person will understand that various steps as described above are mechanistic steps and can be performed simultaneously, such as by performing an alkylation using DMSO at 80° C. in an aqueous environment, resulting in both alkylation and hydrolysis.

Particularly, monomers of general formula (In) generally do not need conversion as they already comprise a ninhydrin type moiety, or they can be converted by dissociation of bound urea. Such dissociation is preferably via incubation with an aqueous solution of at least 6M, preferably 12M hydrohalic acid, preferably HCl. Accordingly, in preferred embodiments, the invention provides the production method according to the invention, wherein step i) comprises the provision of a monomer of general formula (In), and wherein step iii) is absent or comprises converting polymerized monomers of general formula (In) into ninhydrin-type monomers using an aqueous solution of at least 6M, preferably 12M hydrohalic acid, preferably HCl.

Particularly, monomers of general formula (Ip) are generally successfully converted into ninhydrin-type monomers in two steps, using dimethyl sulfoxide (DMSO) and hydrohalic acid such as HCl, HBr, or HI (see Becker and Russell, J. Org. Chem., 1963 DOI: 10.1021/jo01042a502). In such a reaction, condensation of one of the monomer's esters with DMSO in the presence of a base such as alkali metal alkoxides such as sodium methoxide (NaOMe), leads to beta-keto sulfoxides which in the presence of mineral acids undergo the Pummerer rearrangement to give hemimercaptals of alfa-ketoaldehydes. When for example polymerized dimethyl 4-ethenylbenzene-1,2-dicarboxylate is used in this reaction, intramolecular ester condensation leads to formation of an 1,3-indandione system. Acidification with hydrohalic acid such as hydrochloric acid leads to an alfa-halo thioether. The reaction is preferably performed under dry conditions and under an oxygen-free inert atmosphere. The alfa-halo thioether is readily hydrolyzed in boiling water to yield ninhydrin-type moieties in nearly quantitative yields. Monomers of general formula (Ip) comprising free carboxylic acids can be esterified prior to this reaction sequence, for example using methyl halides such as MeI. Anhydrides can be hydrolyzed prior to this. Accordingly, in preferred embodiments, the invention provides the production method according to the invention, wherein step i) comprises the provision of a monomer of general formula (Ip), and wherein step iii) comprises converting polymerized monomers of general formula (Ip) into ninhydrin-type monomers using dimethyl sulfoxide (DMSO) and hydrohalic acid, preferably using DMSO and a hydrohalic acid such as HCl.

Particularly, indanone-type monomers of general formula (Ii) are generally successfully converted into ninhydrin-type monomers in a single oxidation step, preferably using dimethyl sulfoxide (DMSO) and hydrohalic acid such as HCl, HBr, or HI (see example 3.1). In short, a polymer obtained in step ii) comprising monomers of general formula (Ii) can be oxidized by adding aqueous hydrohalic acid such as HI, HCl, or HBr, preferably a mixture of HBr and HI, and a molecular halogen such as $Br_2$, $Cl_2$, or $I_2$, preferably $I_2$. Accordingly, in preferred embodiments, the invention provides the production method according to the invention, wherein step i) comprises the provision of a monomer of general formula (Ii), and wherein step iii) comprises converting polymerized monomers of general formula (Ii) into ninhydrin-type monomers using dimethyl sulfoxide (DMSO) and hydrohalic acid, preferably using DMSO and at least one of HBr and HI. Alternately, monomers of general formula (Ii) can be converted into monomers of general formula (Ip) using acid dichromate ($Cr_2O_7$) salts, after which the conversion reactions described above can be used. Monomers of general formula (Ii) that are not indanone-type monomers can be directly oxidized into indanone-type monomers of general formula (Ii), preferably using an oxide such as $SeO_2$. Accordingly, in preferred embodiments, the invention provides the production method according to the invention, wherein step i) comprises the provision of a monomer of general formula (Ii), and wherein step iii) comprises optionally converting the monomer of general formula (Ii) into an indanone-type monomer of general formula (Ii) by oxidation, and subsequently converting polymerized monomers of general formula (Ii) into ninhydrin-type monomers using dimethyl sulfoxide (DMSO) and hydrohalic acid, preferably using DMSO and at least one of HBr and HI.

In preferred embodiments, the invention provides the production method according to the invention, wherein in step iii) more than 30%, 35%, 40%, 45%, 50%, 55%, 60%, 65%, 70%, 75%, 80%, 85%, 90%, 95%, or 100% of the monomers of general formula (I) are converted into ninhydrin-type monomers. In more preferred embodiments, the invention provides the production method according to the invention, wherein in step iii) more than 55%, 60%, 65%, 70%, 75%, 80%, 85%, 90%, 95%, or 100% of the monomers of general formula (I) are converted into ninhydrin-type monomers. In even more preferred embodiments, the invention provides the production method according to the invention, wherein in step iii) from 55% to 100% of the monomers of general formula (I) are converted into ninhydrin-type monomers. In most preferred embodiments, the invention provides the production method according to the invention, wherein in step iii) from 55% to 90% of the monomers of general formula (I) are converted into ninhydrin-type monomers.

In particular embodiments of the invention, in step iii) 0% of the monomers of general formula (I) are converted into ninhydrin-type monomers. This is particularly the case when all polymerized monomers of general formula (I) already are ninhydrin-type monomers.

Composition and Other Products

In a third aspect of the invention, the invention provides a composition comprising the ninhydrin-type sorbent according to the invention and a pharmaceutically acceptable excipient. Such a composition is referred to hereinafter as a composition according to the invention. Such a composition is preferably a pharmaceutically composition.

Compositions and pharmaceutical compositions according to the invention may be manufactured by processes well known in the art; e.g., by means of conventional mixing, dissolving, granulating, dragee-making, levigating, emulsifying, encapsulating, entrapping or lyophilizing processes, which may result in liposomal formulations, coacervates, oil-in-water emulsions, nanoparticulate/microparticulate powders, or any other shape or form. Compositions for use in accordance with the invention thus may be formulated in conventional manner using one or more physiologically acceptable carriers comprising excipients and auxiliaries that facilitate processing of the active compounds into preparations which can be used pharmaceutically. Proper formulation is dependent on the route of administration chosen.

Oral and parenteral administration may be used wherein the compound or composition according to the invention can be formulated readily by combining a compound or composition according to the invention with pharmaceutically acceptable carriers well known in the art, or by using a compound or composition according to the invention as a food additive. Such strategies enable the compounds or compositions according to the invention to be formulated as tablets, pills, dragees, capsules, liquids, gels, syrups, slurries, suspensions and the like, for oral ingestion by a subject to be treated. Preparations or pharmacological preparations for oral use can made with the use of a solid excipient, optionally grinding the resulting mixture, and processing the mixture of granules, after adding suitable auxiliaries, if desired, to obtain tablets or dragée cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinyl pyrrolidone, agar, or alginic acid or a salt thereof such as sodium alginate. Additionally, coformulations may be made with uptake enhancers known in the art.

Alternatively, one or more components of the composition may be in powder form for constitution with a suitable vehicle, e.g., sterile pyrogen-free water, before use. Components of the composition may be supplied separately.

The compositions or pharmaceutical compositions according to the invention also may comprise suitable solid or gel phase carriers or excipients. Examples of such carriers or excipients include but are not limited to calcium carbonate, various sugars, starches, cellulose derivatives, gelatin, and polymers such as polyethylene glycols.

A pharmaceutical composition according to the invention can also comprise a further pharmaceutically active substance, preferably a further pharmaceutically active substance for the treatment of a disease or condition associated with accumulation of urea or with improper clearance of urea, such as acute kidney failure or end stage kidney disease (ESKD).

A composition according to the invention or a ninhydrin-type sorbent according to the invention can advantageously be used in renal replacement therapy, such as peritoneal dialysis or hemodialysis. During such use, the sorbent or composition is generally present in a cartridge or membrane, which can be replaceably inserted in a (hemo)dialysis device. Accordingly, the invention provides a cartridge for use in a dialysis device, comprising a ninhydrin-type sorbent according to the invention, or comprising a composition according to the invention. Such a dialysis device can be a hemodialysis device or a device for regeneration of peritoneal dialysate in peritoneal dialysis. Accordingly, the invention provides a membrane for use in a dialysis device, comprising a ninhydrin-type sorbent according to the invention, or comprising a composition according to the invention. Such a dialysis device can be a hemodialysis device or a device for regeneration of peritoneal dialysate in peritoneal dialysis. Accordingly, the invention provides a dialysis device comprising a ninhydrin-type sorbent according to the invention, a composition according to the invention, or a cassette according to the invention. Such a dialysis device can be a hemodialysis device or a device for regeneration of peritoneal dialysate in peritoneal dialysis.

Besides the ninhydrin-type sorbent according to the invention, or the composition according to the invention, as comprised in the cartridge, the membrane, or the dialysis device, such cartridges, membranes, and dialysis devices are known in the art. In particular embodiments, the cartridge is a disposable cartridge. In particular embodiments, the cartridge is a regenerable cartridge. Cartridges can also be referred to as cassettes. The cartridge is preferably adaptable to be used with various different types of components and to be arranged in a variety of ways. A cartridge may comprise further sorbents. By removing nucleophilic waste solutes, the cartridge at least partially regenerates the dialysate and/or filtrate used during dialysis. The cartridge preferably includes a body having a fluid inlet and a fluid outlet. The interior of the cartridge is preferably constructed and arranged so that fluid entering the interior from the inlet flows through the sorbent and subsequently through the outlet.

A membrane for use in a dialysis device is preferably semipermeable. It can be sheet-like and separate two volumes by acting as a wall or as part of a wall. It can be in the form of a fibre bundle that connects two volumes. A very suitable fibre bundle is described in WO2006019293, wherein a bundle of hollow or solid fibres having multiple porous layers concentrically arranged is described. In such a bundle one of the layers can comprise functionalized or active particles that are well accessible to the fluids that flow through the membrane. In preferred embodiments of the invention, the ninhydrin-type sorbent according to the invention is comprised in a membrane such as a bundle of fibres wherein the fibres have multiple concentric layers, preferably comprised in one of the layers of such a fibre, preferably configured in such a way that it comes into contact with fluids passing through the membrane, or with fluids that pass through the membrane, preferably further configured to bind nucleophilic waste solutes in said fluids. Such membranes can act as combined membrane and sorbent, allowing further miniaturization.

A dialysis device is a closed, sterile system. It comprises one or two fluid circuits. It usually comprises two circuits: a so-called patient loop, which is a fluid circuit that is arranged for a subject's fluid such as blood or peritoneal dialysate to flow through it, and a so-called regeneration loop, wherein a dialysis fluid such as dialysate and/or filtrate is circulated through a cartridge as described above. The two circuits are separated from each other by a (semi-permeable) membrane, through which waste solutes can diffuse or pass from the subject's fluid into the dialysis fluid. Air, moisture, pathogens, and fluids from the environment around the dialysis device cannot enter into the fluid circuits. The dialysis system only permits fluids (such as ultrafiltrate) and air to exit or enter these fluid circuits under controlled circumstances.

Medical Use

In a fourth aspect the invention provides the medical use of ninhydrin-type sorbents according to the invention, and of compositions according to the invention. As such, this aspect provides a ninhydrin-type sorbent according to the invention, or composition according to the invention, for use as a medicament, preferably for use in the treatment of a disease or condition associated with accumulation of urea or with improper clearance of urea. Such a sorbent or composition is referred to herein as a product for use according to the invention.

In particular embodiments of this aspect, the invention provides a ninhydrin-type sorbent according to the invention, or a composition according to the invention, for use as a medicament for use in the treatment of a disease or condition associated with accumulation of ammonia or with improper clearance of ammonia. In further particular embodiments of this aspect, the invention provides a ninhydrin-type sorbent according to the invention, or a composition according to the invention, for use as a medicament, wherein the ninhydrin-type sorbent is for binding urea. In further particular embodiments of this aspect, the invention provides a ninhydrin-type sorbent according to the invention, or a composition according to the invention, for use as a medicament, wherein the ninhydrin-type sorbent is for binding ammonia.

Treatment of a disease or condition can be the amelioration, suppression, prevention, delay, cure, or prevention of a disease or condition or of symptoms thereof, preferably it shall be the suppression of symptoms of a disease or condition. Urea can accumulate or can be insufficiently cleared in case of kidney failure. Examples of diseases or conditions associated with accumulation of urea or with improper clearance of urea are end stage kidney disease (ESKD); severe acute kidney failure; increased hepatic production of urea for example due to gastro-intestinal haemorrhage; increased protein catabolism, for example due to trauma such as major surgery or extreme starvation with muscle breakdown; increased renal reabsorption of urea, for example due to any cause of reduced renal perfusion, for example congestive cardiac failure, shock, severe diarrhea; iatrogenic conditions due to urea infusion for its diuretic action, due to drug therapy leading to an increased urea production such as treatment with tetracyclines or corticosteroid; chronic kidney failure; and urinary outflow obstruction.

Products for use according to the invention can be administered to a subject in need thereof, allowing the product for use according to the invention to bind nucleophilic waste solutes in the subject. Such administration is preferably administration of an effective amount. The use of other sorbents in such a method is known in the art (Gardner et al., Appl Biochem Biotechnol. 1984; 10:27-40.)

Administration can be via methods known in the art, preferably via oral ingestion in any formulation known in the art such as a capsule, pill, lozenge, gel capsule, push-fit capsule, controlled release formulation, or via rectal administration as a clyster or suppository. It can be once per week, 6, 5, 4, 3, 2, 1 time per week, daily, twice daily, or three times per day, or four times per day.

Products for use according to the invention are suitable for use in a method of treatment. Such a method of treatment can be a method comprising the step of administering to a subject, preferably a subject in need thereof, an amount, preferably an effective amount, of product for use according to the invention.

With respect to dialysis therapy, the present invention can be used in a variety of different dialysis therapies to treat kidney failure. Dialysis therapy as the term or like terms are used throughout the text is meant to include and encompass any and all forms of therapies to remove waste, toxins and excess water from the subject suffering from a disease or condition. The hemo therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. The present invention can also be used during peritoneal dialysis including, for example, continuous ambulatory peritoneal dialysis, automated peritoneal dialysis, continuous flow peritoneal dialysis and the like. Further, although the present invention, in an embodiment, can be utilized in methods providing a dialysis therapy for subjects having acute or chronic kidney failure or disease, it should be appreciated that the present invention can also be used for acute dialysis needs, for example, in an emergency room setting. However, it should be appreciated that the compositions of the present invention can be effectively utilized with a variety of different applications, physiologic and non-physiologic, in addition to dialysis.

Method of Use

The ninhydrin-type sorbents according to the invention are surprisingly effective at binding nucleophilic solutes, preferably nucleophilic waste solutes. In a fifth aspect, the invention provides a method for removing nucleophilic waste solutes from a fluid, comprising the steps of:

i) providing a fluid comprising nucleophilic waste solutes, and iia) contacting said fluid with a ninhydrin-type sorbent according to the invention, or with a composition according to the invention, or with a cartridge according to the invention, or alternately iib) contacting said fluid with a dialysis fluid through a membrane, wherein the dialysis fluid is in contact with a ninhydrin-type sorbent according to the invention, or with a composition according to the invention, or with a cartridge according to the invention, and iii) optionally, recovering the fluid.

Such a method is referred to hereinafter as a binding method according to the invention. The method can be a continuous process, wherein provision of a fluid comprising nucleophilic waste solutes is through provision of a continuous flow of fluid. In such a case, preferably step iii) is not optional, and is also continuously performed. A binding method according to the invention always comprises step i), a step ii) (one of either step iia) or step iib)), and optionally step iii).

Nucleophilic waste solutes are dissolved substances that are nucleophilic, the removal of which is desired. For example, in human blood, urea is a waste solute. In unpurified water intended as drinking water, most organic nucleophiles are waste solutes. Examples of nucleophilic waste solutes are ammonia, urea, creatinine, and small molecule organic amines, thiols, or alcohols. The chemical binding properties make the ninhydrin-type sorbent according to the invention well suited for a variety of different applications subject to physiological and/or non-physiological conditions. In an embodiment, the ninhydrin-type sorbent according to the invention can be used to remove metabolic waste, such as urea, creatinine, uric acid and/or others like uremic toxins, biological matter, proteinaceous matter, and/or the like from blood, peritoneal dialysate, and/or solutions used to dialyze and/or filter blood, such as dialysate and/or filtrate. Due to its relevance as described elsewhere herein, highly preferred nucleophilic waste solutes are urea and ammonia. In preferred embodiments, the nucleophilic waste solute is ammonia. In other preferred embodiments, the nucleophilic waste solute is urea.

In step i) a fluid comprising a nucleophilic waste solute is provided. This can be waste water which is to be purified, it can be waste solvent which is to be purified, but it can also be a (body) fluid from a subject, such as blood or peritoneal dialysate. When the fluid of step i) is a fluid from a subject, it is preferably blood or peritoneal dialysate, most preferably blood, and preferably a fluid that has been previously obtained from a subject.

In step ii), two options exist. In one option, step iia), the fluid itself is directly contacted with the ninhydrin-type sorbent according to the invention, the composition according to the invention, or the membrane or cartridge according to the invention. Step iia) is very suitable for purification of solvents, or for fluids that are not intended for consumption or for medical purposes after removal of the waste solutes. Step iib) separates the binding sorbent from fluid provided in step i) by using dialysis fluid and/or filtrate. Step iib) is particularly suited for the removal of nucleophilic waste solutes from pharmaceutical solutions or from fluids obtained from a subject, such as bodily fluids of a subject. Contacting preferably lasts 24 hours, 12 hours, 6 hours, 4 hours, 3 hours, 2 hours, 60 minutes, 50 minutes, 40 minutes, 30 minutes, 20 minutes, 15 minutes, 10 minutes, 9, 8, 7, 6, 5, 4, 3, 2, or 1 minutes, or less. Contacting can also be in continuous flow past the sorbent, in which case the total amount of removed waste solute is more relevant.

Membranes for use in step iib) are preferably semipermeable membranes. These are known in the art, and can for example be the semipermeable membrane present in a conventional (hemo)dialysis device. Membranes according to the invention as described above can also be used. Dialysis fluids are known in the art and can range from ultrapure water to physiological buffers. Non-limiting examples of dialysis fluids are media comprising known amounts of for example Na, K, Ca, Mg, Cl, acetate, $HCO_3$, and glucose, such as those available from MDN Neubrandenburg GmbH (Neubrandenburg, Germany), or from Baxter (Deerfield, Ill., USA), or from Dirinco B.V. (Oss, the Netherlands).

In step iii), which is optional, the fluid is recovered. The ninhydrin-type sorbent according to the invention is often porous, macroporous, or swellable in aqueous media, such that fluids can flow through it and permeate it. Recovery of a fluid that has been contacted with a sorbent is readily achieved by filtration, centrifugation, or removal of the cartridge containing the sorbent. Recovery of a fluid allows its further processing, or its return to a subject. In preferred embodiments within this aspect, the fluid is recovered.

Preferably, when a fluid is recovered in step iii), relevant physiological parameters are subsequently analyzed and adjusted when appropriate. Examples are ion concentrations, osmolality, pH, particularly Na concentration, Ca concentration, and Mg concentration. Accordingly, a preferred step iii) is the step of recovering the fluid, after which at least one of fluid pH, fluid sodium concentration, fluid magnesium concentration, and fluid calcium concentration is determined and optionally adjusted to a reference value. Preferred reference values are corresponding physiological values for the fluid type. The adjustment can be done in any suitable way known in the art. The adjustment is preferably performed when a deviation from the reference value is detected.

In preferred embodiments of the binding method, at least 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.67, 1.68, 1.69, 1.70, 1.71, 1.72, 1.73, 1.74, 1.75, 1.76, 1.77, 1.78, 1.79, 1.80, 1.85, 1.90, 1.95, 2.00, 2.05, 2.10, 2.15, 2.20, 2.25, 2.30, 2.35, 2.40, 2.45, or 2.50 mmol of nucleophilic waste solute per gram of sorbent is removed; more preferably at least 2.10, 2.15, 2.20, 2.25, 2.30, 2.35, 2.40, 2.45, or 2.50 mmol of nucleophilic waste solute per gram of sorbent is removed. This removal preferably entailed removal of at least 10%, 20%, 30%, 40%, 50%, 60%, 70%, 80%, 85%, 90%, 91%, 92%, 93%, 94%, 95%, or more of a particular nucleophilic waste solute's initial concentration from a fluid as provided in step i), more preferably removal of at least 50% or more.

The reaction between the ninhydrin-type sorbent according to the invention and many different nucleophilic waste solutes is a reversible reaction. Because of ninhydrin's reactivity, it forms hemiaminal moieties upon reaction with for example urea, and such hemiaminals can be dissociated into their original components. As a result, the ninhydrin-type sorbent can be regenerated for repeated use. Therefore, the invention provides a method for regenerating a ninhydrin-type sorbent according to the invention, or a cartridge according to the invention, comprising the steps of:

i) contacting the ninhydrin-type sorbent with an acidic regeneration solution;

ii) optionally, heating the regeneration solution while it is in contact with the ninhydrin-type sorbent;

iii) recovering the ninhydrin-type sorbent from the regeneration solution; and iv) optionally, washing the ninhydrin-type sorbent.

This method is referred to as a regeneration method according to the invention In preferred embodiments, the regeneration method according to the invention is for regenerating a ninhydrin-type sorbent that has bound a nucleophilic waste solute, or more preferably that has bound urea. Regeneration, in the context of this invention, refers to the reversal of the binding reaction between the ninhydrin-type sorbent and the nucleophilic waste solute. In other words, it refers to the reformation of ninhydrin-type moieties.

In step i) an acidic regeneration solution is used. Preferred acidic regeneration solutions are acidic aqueous regeneration solutions. Examples of suitable acidic regeneration solutions are aqueous hydrohalic acid solutions such as HCl, $HClO_4$ (perchloric acid, referred to as PCA), HBr, and HI, preferably HCl or PCA, or sulfuric acid solutions. Such solutions, preferably HCl, are preferably at least 6M, more preferably they are 8M or 10M, most preferably 12M. For $H_2SO_4$, the solution is preferably 2M to 10M, more preferably 3M to 9M. For PCA, the solution is preferably 2M to 9M, more preferably 2M to 8M, even more preferably 3M to 8M, most preferably 6M to 8M, such as about 6M. A preferred regeneration solution is an aqueous HCl or PCA solution of at least 6M such as of about 6M. A more preferred regeneration solution is an aqueous HCl solution of at least 12M or an aqueous PCA solution of 6M to 8M, preferably of about 6M.

In step ii), which is optional, the regeneration solution is heated while it is in contact with the ninhydrin-type sorbent that is to be regenerated. The heating of step ii) can accelerate the regeneration, generally by increasing the reaction rate of the reversal reaction. In preferred embodiments the regeneration solution is heated to at least 40, 45, 50, 55, 60, 65, 70, 75, 80, 85, 90, 95, or 100° C., more preferably to at least 40 to 70° C. Most preferably the regeneration solution is heated to about 70° C.

In step iii), the ninhydrin-type sorbent is recovered from the regeneration solution. This ninhydrin-type sorbent is now a regenerated ninhydrin-type sorbent. In preferred embodiments, at least 10%, 20%, 30%, 40%, 50%, 60%, 70%, 80%, 85%, 90%, 91%, 92%, 93%, 94%, 95%, or more of the original ninhydrin-type moiety content has been regenerated. More preferably, at least 70%, 80%, or 90% of the original ninhydrin-type moiety content has been regenerated, most preferably at least 80% of the original ninhydrin-type moiety content has been regenerated. In further preferred embodiments at least 19% or more of the original ninhydrin-type moiety content has been regenerated; more preferably at least 25%, even more preferably at least 26% or 27%, most preferably at least 30%, 35%, 39%, or 46% of the original ninhydrin-type moiety content has been regenerated.

In step iv), which is optional, the ninhydrin-type sorbent is washed. Washing can be done with any type of solvent or solution, preferably using water or a mixture of water and DMSO or a mixture of water and acetone, most preferably using water. The washing is to remove liberated nucleophilic waste solutes, and to remove regeneration solution from the ninhydrin-type sorbent. Washing can be repeated more than once. Washing can advantageously be performed on a filter, such as on a fritted syringe barrel used in solid phase peptide synthesis, or in a column.

General Definitions

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value more or less 1% of the value.

Molecules provided in this invention can be optionally substituted. Suitable optional substitutions are replacement of —H by a halogen. Preferred halogens are F, Cl, Br, and I. Further suitable optional substitutions are substitution of one or more —H by —$NH_2$, —OH, =O, alkyl, alkoxy, haloalkyl, haloalkoxy, alkene, haloalkene, alkyn, haloalkyn, and cycloalkyl. Alkyl groups have the general formula $C_nH_{2n+1}$ and may alternately be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc.

Unless stated otherwise, —H may optionally be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^2)_3Si$—, wherein $R^2$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one or more hetero-atoms selected from the group consisting of O, N and S.

When a structural formula or chemical name is understood by the skilled person to have chiral centers, yet no chirality is indicated, for each chiral center individual reference is made to all three of either the racemic mixture, the pure R enantiomer, and the pure S enantiomer. When two moieties are said to together form a bond, this implies the absence of these moieties as atoms, and compliance of valence being fulfilled by a replacing electron bond. All this is known in the art.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components. It is understood that charge is often associated with equilibrium. A moiety that is said to carry or bear a charge is a moiety that will be found in a state where it bears or carries such a charge more often than that it does not bear or carry such a charge. As such, an atom that is indicated in this disclosure to be charged could be non-charged under specific conditions, and a neutral moiety could be charged under specific conditions, as is understood by a person skilled in the art.

In the context of this invention, a decrease or increase of a parameter to be assessed means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

The use of a substance as a medicament as described in this document can also be interpreted as the use of said substance in the manufacture of a medicament. Similarly, whenever a substance is used for treatment or as a medicament, it can also be used for the manufacture of a medicament for treatment. Products for use are suitable for use in methods of treatment.

Throughout this invention, when percentages are used for expressing amounts of monomers and comonomers in a mixture, mole percentages are intended, unless stated otherwise or explicitly plain from context.

Throughout this application, (hemo)dialysis refers to both hemodialysis and dialysis. In general, a dialysis device can refer to any type of dialysis device as described herein.

The present invention has been described above with reference to a number of exemplary embodiments. Modifications and alternative implementations of some parts or elements are possible, and are included in the scope of protection as defined in the appended claims. All citations of literature and patent documents are hereby incorporated by reference.

Figure 1:
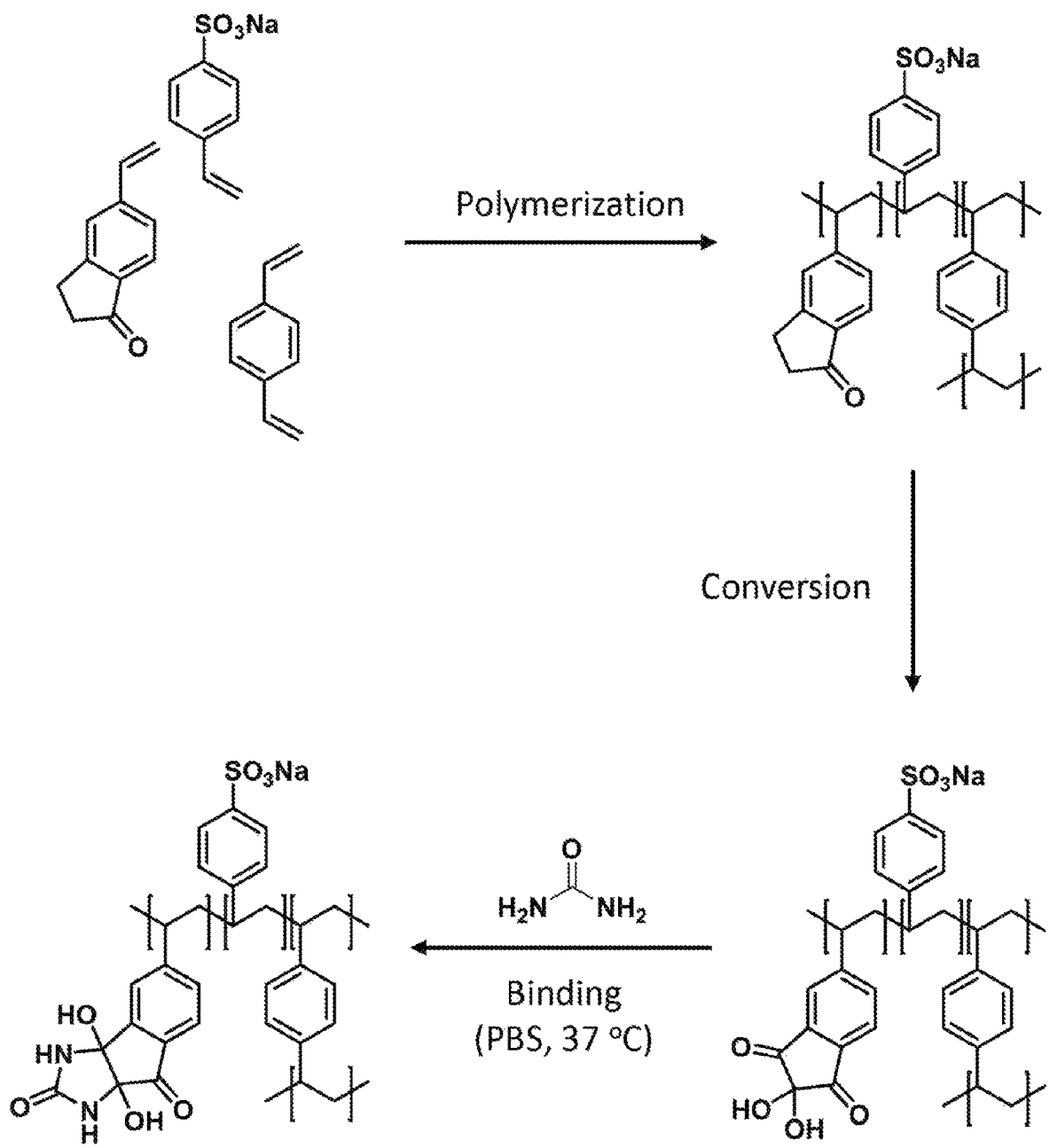
FIG. 1—general strategy for the preparation of ninhydrin-type sorbents using the production method according to the invention. In this figure, 5-ethenylindane-2-one is used as the monomer of general formula (I), and comonomers sodium styrene sulfonate and 1,4-divinylbenzene are present. The sorbents can then be used to capture nucleophilic waste solutes such as urea, under physiologically relevant conditions (a PBS buffer at 37° C.).

3A; B) spectrum urea bound to a sorbent according to the invention, showing the same characteristic signal as the reference spectrum.

FIG. 5—FTIR spectroscopic analysis of sorbent regeneration of sorbent with a 70:30 feed ratio of ninhydrin:styrene sulfonate. A) reference spectrum of free sorbent; B) spectrum of sorbent saturated with urea; C) spectra of regeneration conditions that did not lead to acceptable levels of regeneration, using PBS, 0.2M HCl, 2M HCl, or 6M HCl as indicated; D) spectra of regeneration conditions that led to acceptable levels of regeneration, using 12M HCl or using repeated treatments with 6M HCl (3 repeats).

EXAMPLES

Example 1—Provision of Monomers

General Method for Providing Monomers of General Formula (I)

Monomers can be purchased from commercial suppliers when available, or can be prepared by chemical synthesis. For this, metal-catalysed cross-coupling reactions are suitable, starting from halo-derivatives of indenes, indanones, or phthalic acid derivatives that are generally commercially available. The Sonogashira coupling is particularly suitable for introducing vinyl (ethenyl) moieties, using a halo-derivative as described above, and trimethylsilylacetylene with a palladium catalyst and a copper catalyst. After the coupling, deprotection of the trimethylsilylacetylene (TMS) group and partial hydrogenation using Lindlar's catalyst provides the ethenyl-monomer of general formula (I) with high overall yield. For 2-propenyl monomers, other cross-coupling reactions can be used, such as a Stille coupling using 2-propenyl-SnBu$_3$ and a halo-derivative as described above, for example using PhCH$_2$Pd(PPh$_3$)$_2$Cl as a catalyst. Suitable cross-coupling reactions are known to a skilled person, and can be found for example in handbooks such as "Metal-Catalyzed Cross-Coupling Reactions, Second Edition" (2008) DOI: 10.1002/9783527619535.

Synthesis of 5-ethenylindane-1-one 1.1 2,3-dihydro-5-[2-(trimethylsily)ethynyl]inden-1-one

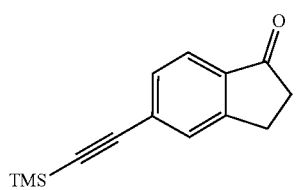 [SMILES: C[Si](C)(C)C#Cc1ccc2c(c1)CCC2=O]

In a flame-dried 3-neck round bottom flask under nitrogen atmosphere, to a mixture of 5-bromo-1-indanone (7.0 g, 33.3 mmol), (Ph$_3$P)$_2$PdCl$_2$ (232 mg, 1 mol %,) and CuI (126 mg, 2 mol %) in 3:1 anhydrous Et$_3$N:DMF (55 mL) trimethylsilylacetylene (6.8 mL, 50 mmol) was added dropwise. The reaction was then heated to 80° C. for 2 h. The reaction mixture was allowed to cool to RT and was transferred to a seperation funnel. The mixture was extracted with water and CH$_2$Cl$_2$. The combined organic layers were washed with 10% HCl, 10% Na$_2$CO$_3$, and water (10 mL) and then dried over Na$_2$SO$_4$, filtrated and concentrated. The residue was purified by flash chromatography (4:1 EtOAc:hexane), and 2,3-dihydro-5-[2-(trimethylsilyl)ethynyl]inden-1-one (7.09 g, 93%) was isolated as a solid. $^1$H NMR (CDCl$_3$) δ: 7.68 (d, 1H, J=8.2), 7.57 (s, 1H), 7.44 (dd, 1H, J=8.1,0.7), 3.14-3.10 (m, 2H), 2.73-2.68 (m, 2H), 0.26 (s, 9H).

1.2 5-ethynylindane-1-one

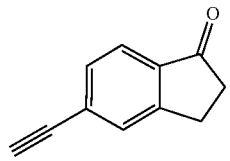

A mixture of 2,3-dihydro-5-[2-(trimethylsilyl)ethynyl]inden-1-one (6.8 g, 30 mmol) and K$_2$CO$_3$ (2.0 g, 15 mmol) in MeOH (35 mL) was stirred at RT for 2 h. The reaction mixture was concentrated and extracted with CH$_2$Cl$_2$ and water. The organic extract was washed with water and brine (5 mL), and dried over Na$_2$SO$_4$. After filtration the mixture was concentrated under reduced pressure, and the crude product was purified by chromatography on silica gel (4:1 EtOAc/hexane). 5-ethynylindane-1-one was isolated as a brown solid (4.3 g, 92%). $^1$H NMR (CDCl$_3$) δ: 7.70 (dd, 1H, J=7.7,0.6), 7.60 (s, 1H), 7.47 (d, 1H, J=8.8), 3.25 (s, 1H), 3.15-3.11 (m, 2H), 2.73-2.71 (m, 2H).

1.3 5-ethenylindane-1-one

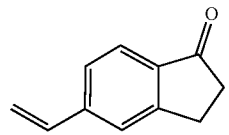

5-ethynylindane-1-one (3.7 g, 23.6 mmol) was suspended in EtOH (100 mL) and Lindlar's catalyst (3%) was added. The reaction was capped with a septum and the air was replaced with H$_2$ (balloon), after which the reaction was stirred vigorously overnight. The reaction was filtrated over kieselgur (hiflo) packed with EtOAc and washed with EtOAc. The filtrate was concentrated under reduced pressure and 5-ethenylindane-1-one was furnished as a yellowish solid 3,6 g, 97%. $^1$H NMR (CDCl$_3$) δ: 7.71 (d, J=8.0 Hz, 1H), 7.48 (s, 1H), 7.42 (d, J=8.0 Hz, 1H), 6.78 (dd, J=18.0, J=10.9, 1H), 5.90 (d, J=17.6 Hz, 1H), 5.42 (d, J=10.9 Hz, 1H), 3.13 (m, 2H), 2.70 (m, 2H).

Synthesis of 5-ethenyl-2,2-dihydroxyindane-1,3-dione 1.4 5-ethenyl-2,2-dihydroxyindane-1,3-dione

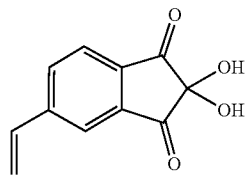

In a method similar to that reported by Marminon et al., (2015, DOI: 10.1016/j.tetlet.2015.02.086) 5-ethenylindane-1-one as obtained from example 1.3 (1.5 mmol, 1 eq.) was dissolved in a 10:1 (vol:vol) mixture of dioxane (4.5 mL) and $H_2O$ (0.45 mL) in a microwave tube equipped with a magnetic stirrer. Selenium dioxide (3.1 eq.) was added and the tube was sealed. The mixture was shaken vigorously and placed in the microwave where it was heated for 5 minutes at 180° C. The crude reaction mixture was impregnated on silica and purified over a silica column (hexane:EtOAc 3:1), yielding the product as a 2:1 mixture of the ninhydrin: indanetrione as a brown oil in a 14% yield.

Synthesis of Dimethyl 4-vinylphthalate 1.5 Dimethyl 4-((trimethylsilyl)ethynyl)phthalate

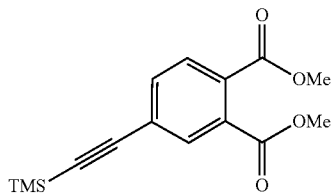 [SMILES: COC(=O)c1ccc(C#C[Si](C)(C)C)cc1C(=O)OC]

In a flame-dried 3-neck round bottom flask under nitrogen atmosphere, to a mixture of dimethyl 4-bromophthalate (5.461 g, 20.0 mmol), $(Ph_3P)_2PdCl_2$ (140 mg, 1 mol %,) and CuI (76 mg, 2 mol %) in 3:1 anhydrous $Et_3N$:DMF (80 mL) trimethylsilylacetylene (4.2 mL, 30 mmol) was added dropwise. The reaction was then heated to 80° C. for 2h. The reaction mixture was allowed to cool to room temperature and was transferred to a seperation funnel. The mixture was extracted with water and $CH_2Cl_2$. The combined organic layers were washed with 10% HCl, 10% $Na_2CO_3$, and water (10 mL) and then dried over $Na_2SO_4$, filtrated, and concentrated. The residue was purified by flash chromatography (5:1 EtOAc:hexane), and dimethyl 4-((trimethylsilyl)ethynyl)phthalate (4.68 g, 81%) was isolated as a yellow liquid. $^1$H NMR (CDCl$_3$) δ: 7.78 (d, J=1.4 Hz, 1J), 7.68 (d, J=8.0 Hz, 1H), 7.58 (dd, J=8.0 Hz, 1.4 Hz, 1H), 3.90 (s, 3H), 3.90 (s, 3H), 0.25 (s, 9H).

1.6 Dimethyl 4-ethynylphthalate

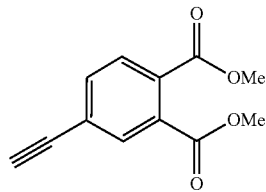 [SMILES: C#Cc1ccc(C(=O)OC)c(C(=O)OC)c1]

A mixture of dimethyl 4-((trimethylsilyl)ethynyl)phthalate (4.065 g, 14 mmol) and $K_2CO_3$ (967 mg, 7 mmol) in MeOH (28 mL) was stirred at room temperature for 10 minutes. The reaction mixture was concentrated and extracted with $CH_2Cl_2$ and water. The organic extract was washed with water and brine (5 mL), and dried over $Na_2SO_4$. After filtration the mixture was concentrated under reduced pressure, and the crude product was purified by chromatography on silica gel (4:1 EtOAc/hexane). Dimethyl 4-ethynylphthalate was isolated as a yellow liquid (2.37 g, 77%). $^1$H NMR (CDCl$_3$) δ: 7.81 (d, J=1.4 Hz, 1H), 7.69 (d, J=8.0 Hz, 1H), 7.62 (dd, J=8.0 Hz, 1.4 Hz, 1H), 3.91 (s, 3H), 3.90 (s, 3H), 3.23 (s, 1H).

1.7 Dimethyl 4-vinylphthalate

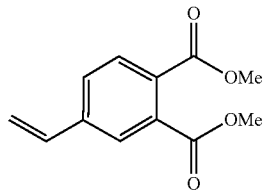 [SMILES: C=Cc1ccc(C(=O)OC)c(C(=O)OC)c1]

Dimethyl 4-ethynylphthalate (2.23 g, 10.3 mmol) was dissolved in EtOH (30 mL) and Lindlar's catalyst (67 mg, 3%) was added. The reaction was capped with a septum and the air was replaced with $H_2$ (balloon), after which the reaction was stirred vigorously for 90 minutes. The reaction was filtrated over kieselgur (hiflo) packed with $CH_2Cl_2$ and washed with $CH_2Cl_2$. The filtrate was concentrated under reduced pressure and dimethyl 4-vinylphthalate was furnished as a yellow liquid 2,08 g, 92%. $^1$H NMR (CDCl$_3$) δ 7.73 (d, J=7.9 Hz, 1 H), 7.69 (d, J=1.7 Hz, 1H), 7.53 (dd, J=7.9 Hz, 1.7 Hz, 1H), 6.73 (dd, J=17.6 Hz, 10.9 Hz, 1H), 5.88 (d, J=17.6 Hz, 1H), 5.42 (d, J=10.9 Hz, 1H), 3.92 (s, 3H), 3.90 (s, 3H).

Example 2—Polymerization

General Method for Polymerization

Polymerization of monomers of general formula (I) can be performed using any known polymerization method, such as ionic polymerization (anionic, cationic), free radical polymerization, or controlled radical polymerization (RAFT, ATRP). Any sufficiently inert dissolving solvent can be used. Suspension polymeriszation is an attractive method because it can lead to granulated material. When a crosslinked sorbent is desired, up to 10% crosslinker can be added to the monomer mixture prior to polymerization, such as a divinylbenzene or butadiene. A skilled person can select suitable crosslinkers, which generally have more than one polymerizable moiety. Using about 0.5% to about 4% crosslinker gave good results. When a more hydrophilic sorbent is desired, hydrophilic comonomers can be added to the monomer mixture prior to polymerization, such as vinylbenzene-sulfonic acid or acrylic acid. A skilled person can select suitable hydrophilic comonomers, which generally have a single polymerizable moiety and which also comprise a very polar group such as a carboxylic acid or a sulfonic acid. Because the polydispersity of the sorbent is not of high importance, it is efficient to let the polymerization run to completion, for example by letting it react overnight. This achieves high monomer economy and reduces the need for reaction monitoring. Purification can be done by precipitation in any solvent in which unreacted substances will dissolve, such as methanol. Alternately, the polymerization mixture can be used in the conversion as a crude mixture.

2.1 Preparation of poly[(5-ethenylindane-2-one)-co-(styrene sulfonate)-co-(divinylbenzene)]

Vinylindanone (0 to 1.0 mmol, 1 eq.) and sodium styrene sulfonate (0 to 1.0 mmol) were dissolved in DMSO (3 mL)

and water (0.75 mL) and 1,4-divinylbenzene (DVB, 0.02 mmol, 3.5 µL) and potassium persulfate ($K_2S_2O_8$, also known as KPS, 0.02 mmol, 5.4 mg) were added, such that a total of 1.02 mmol of monomers was present. $N_2$ was bubbled through the mixture for 15 minutes and the reaction was then stirred at 70° C. overnight (at least about 12 hours). The crude mixture was used in a next reaction without further purification.

2.2 General Solution Polymerisation Method

Monomer (0.5 mmol) was dissolved in EtOH (2-10 mL) and divinylbenzene (1-4 eq.) and AIBN (1-3 mol %) were added. The flask was sealed and nitrogen was bubbled through the solution for 20 minutes. The solution was heated to 60° C. for 24 hours. The mixture was allowed to cool to room temperature and was centrifuged and the supernatant was removed. The resulting sorbent was washed and centrifuged with the EtOH 3 times and the last time washed with water. After centrifugation, the polymer was dried overnight over $P_2O_5$ under vacuum. Exemplary sorbents prepared using this method are listed in table 5.

2.3 General Suspension Polymerisation Method

NaCl (10.5 mg), polyacrylic acid sodium salt (468 mg of a 10 w % gel in water), and $Ca_3(PO_4)_2$ (86 mg) were added to water (15 mL) in a glass reactor with mechanical stirrer, and stirred for 30 minutes. Monomer (15 mmol), porogen (2-3 mL of a non-water-miscible liquid), 80% divinylbenzene (1-6 mol %) and 50% benzoylperoxide blend with dicyclohexyl phthalate (1 mol %) were mixed separately and, after the initiator was dissolved, added to the aqueous phase. The mixture was stirred with a mechanical stirrer until an emulsion was obtained. Air was displaced by nitrogen in the glass reactor. The mixture was stirred at 73° C. for 16 hours, after which the suspension was filtered over a 200 µm filter. The resulting powder or beads in the residue were washed with acetone and water and dried over $P_2O_5$ under vacuum. Exemplary sorbents prepared using this method are listed in table 5.

Example 3—Conversion of Polymerized Monomers

General Methods for Conversion of Monomers of General Formula (I)

Polymerization of monomers of general formula (I) can be performed using any known polymerization method, such as ionic polymerization (anionic, cationic), free radical polymerization, or controlled radical polymerization (RAFT, ATRP). When a crosslinked sorbent is desired, up to 10% crosslinker can be added to the monomer mixture prior to polymerization, such as a divinylbenzene or butadiene. A skilled person can select suitable crosslinkers, which generally have more than one polymerizable moiety. Using about 0.5% to about 4% crosslinker gave good results. When a more hydrophilic sorbent is desired, hydrophilic comonomers can be added to the monomer mixture prior to polymerization, such as vinylbenzenesulfonic acid or acrylic acid. A skilled person can select suitable hydrophilic comonomers, which generally have a single polymerizable moiety and which also comprise a very polar group such as a carboxylic acid or a sulfonic acid. Because the polydispersity of the sorbent is not of high importance, it is efficient to let the polymerization run to completion, for example by letting it react overnight. This achieves high monomer economy and reduces the need for reaction monitoring. Purification can be done by precipitation in any solvent in which unreacted substances will dissolve, such as methanol. Alternately, the polymerization mixture can be used in the conversion as a crude mixture. Table 1 shows suitable conversion methods for different monomers of general formula (I).

TABLE 1 suitable conversion methods for different monomers of general formula (I)

| Monomer type | Conversion method |
|---|---|
| 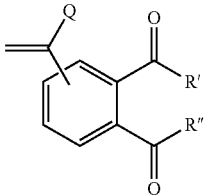<br>(Ip) phthalic-type* | i) Alkylation, preferably using DMSO or ethyl acetoacetate, and optionally a hydrohalic acid such as HBr, HI, or HCl;<br>ii) hydrolysis, preferably by heating to about 80° C. in an aqueous environment. |
| 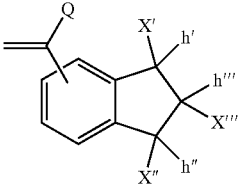<br>(Ii) indene-type* | i) Optional conversion into an indanone-type monomer by oxidation, preferably using an oxide such as $SeO_2$;<br>ii) Conversion using dimethyl sulfoxide (DMSO) and hydrohalic acid<br>iii) hydrolysis |
| 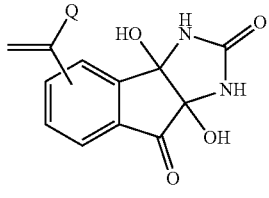<br>(In) with bound urea* | Treatment with hydrohalic acid |
| 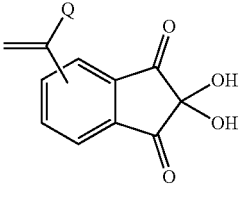<br>Ninhydrin-type* | None required |

*Q, R', R'', X'X'' X''', h'h'', and h''' are as defined elsewhere

3.1 Preparation of poly[(ninhydrine)-co-(styrene sulfonate)-co-(divinylbenzene)]

Figure 2:
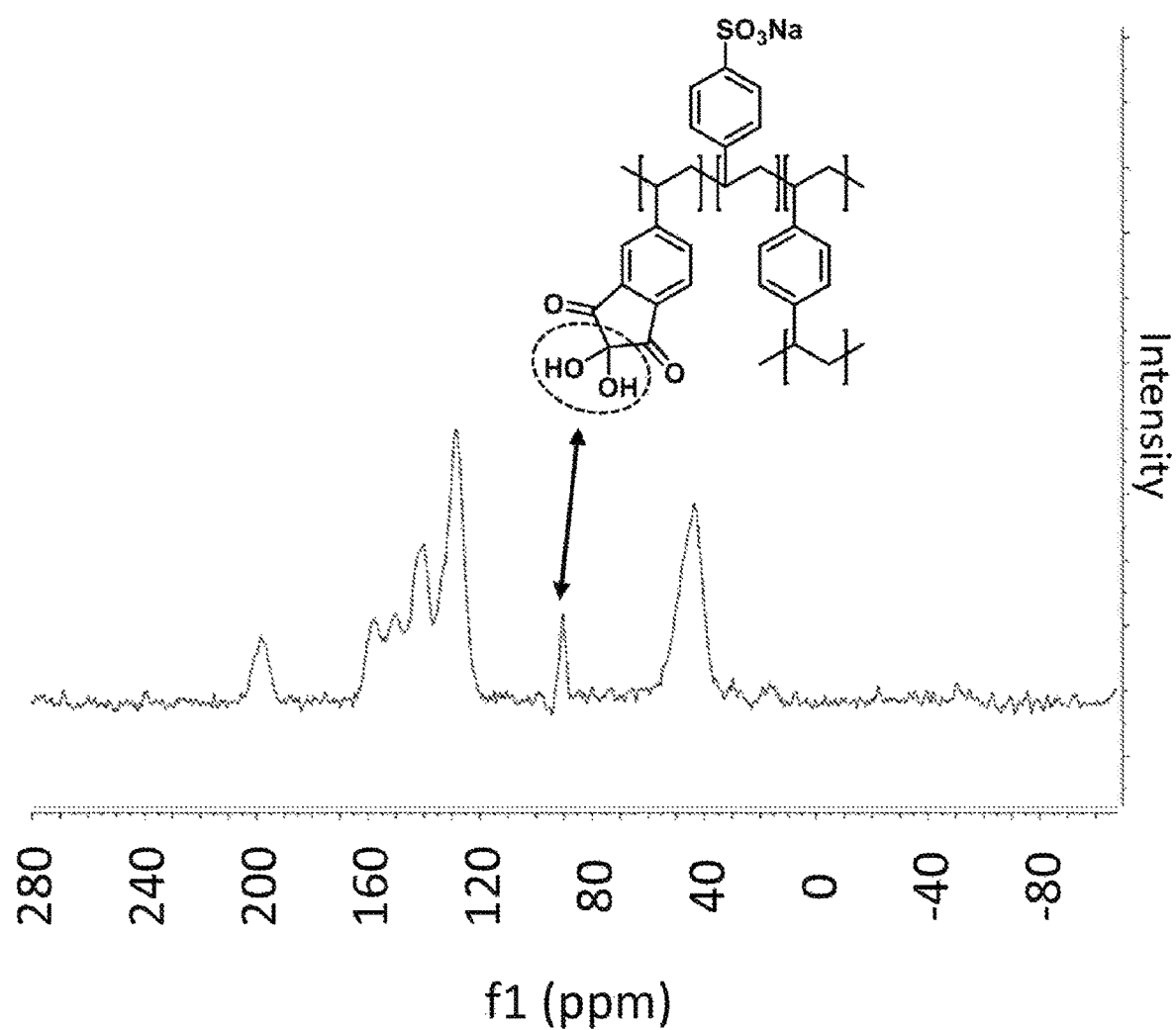
FIG. 2—solid state NMR of the sorbent prepared in example 3.1, comprising ninhydrin-type monomer, a cross-linker and a hydrophilic comonomer. The characteristic peak of the ninhydrin's hydrate is indicated by the arrow.
Figure 3A:
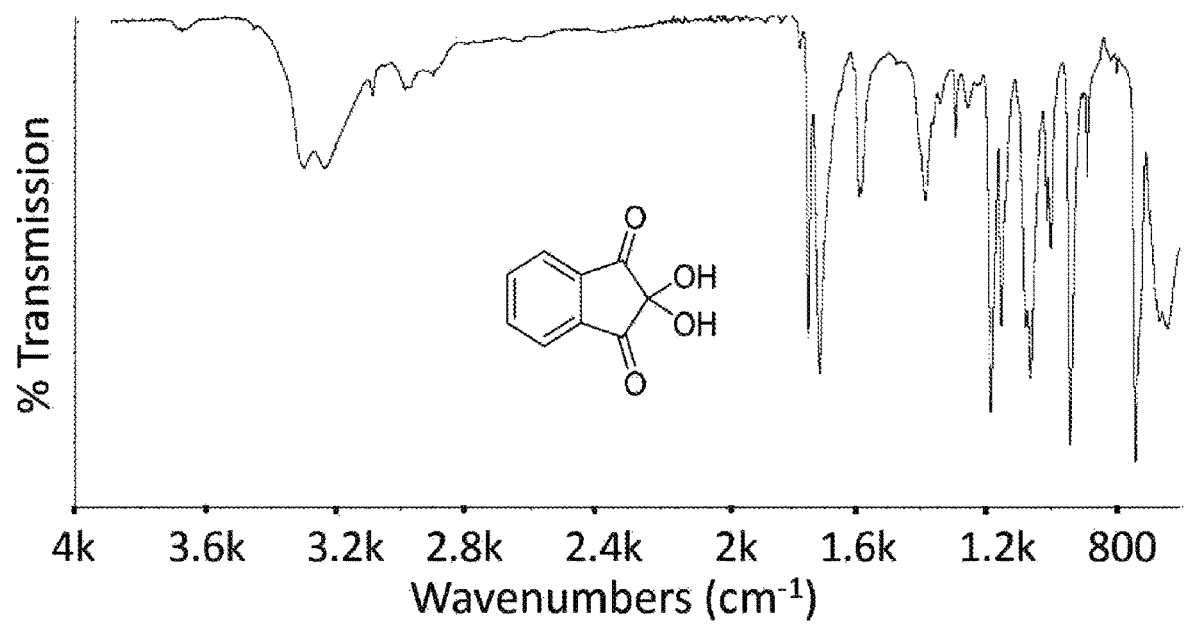
FIG. 3—FTIR spectroscopic analysis of the sorbent prepared in example 3.1. A) reference spectrum of ninhydrin shows a characteristic signal in the 1700 $cm^{-1}$ region; B) spectrum of the sorbent prepared in example 3.1, showing the same characteristic signal as the reference spectrum.
Figure 3B:
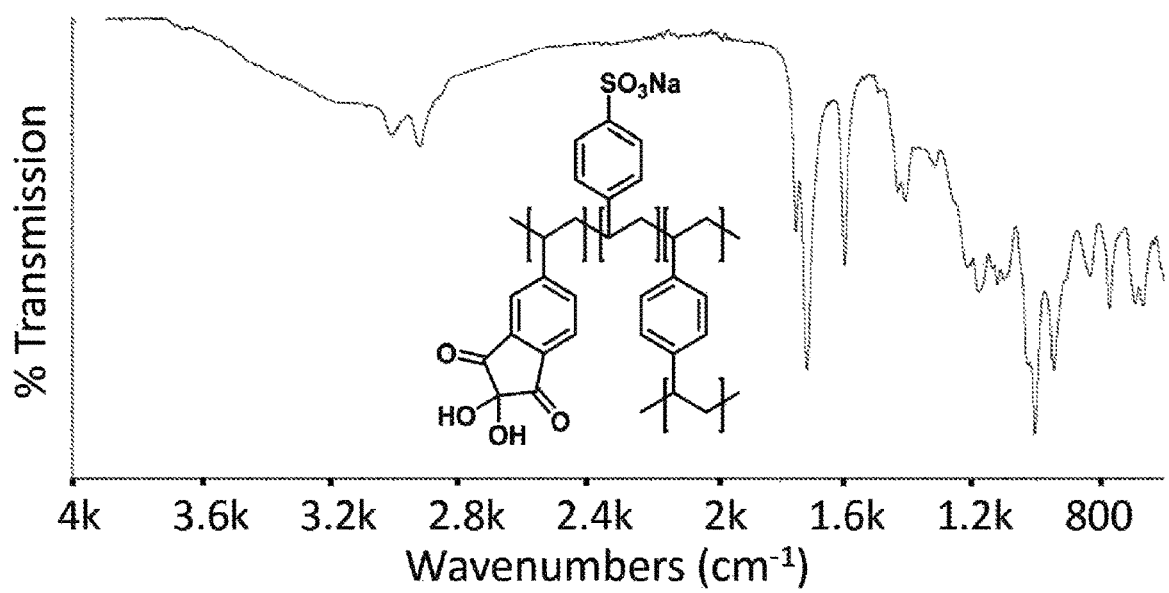

The mixture obtained in example 2.1 was directly oxidized without further purification by adding 48% HBr in water (6 eq.), 57% HI in water (0.2 eq.), and $I_2$ (0.2 eq.). A needle was placed though the septum so evolving $Me_2S$ could escape and the mixture was then placed at 80° C. After 24 hours the mixture was transferred to a dialysis bag (any molecular weight cut off is suitable, as small molecules are to be separated from macromolecules) and the mixture was first dialyzed against DMSO for 3 hours, and then against water overnight. The aqueous mixture was lyophilized, furnishing the sorbent as a foam. The polymers were characterized by solid state NMR (FIG. 2) and by IR spectroscopy (FIG. 3).

3.2 Preparation of poly(ninhydrine) Based on poly(indanone)

Polymer beads obtained via the general suspension polymerisation method described above (500 mg, 2.8 mmol indanone functionality) were swollen in DMSO and stirred with a mechanical stirrer. Aqueous 48% HBr (1.9 mL, 16.8 mmol, 6.0 eq.) was added slowly, followed by iodine (711 mg, 2.8 mmol, 1.0 eq.) and aqueous 57% HI (0.32 mL, 2.8 mmol, 1.0 eq.). The resulting suspension was heated at 90° C. for 24-32 hours. Afterwards the suspension was filtered and the residue was washed with acetone and water and dried over $P_2O_5$ under vacuum.

3.3 Preparation of poly(ninhydrine) Based on poly(phtalic ester)

Similar to a known procedure (H.-D. Becker, G. A. Russell, J. Org. Chem. 28(7) (1963) 1896-1896) sodium methoxide (100 mmol) is suspended in anhydrous DMSO (75 mL) under $N_2$. Sorbent containing phtalic ester (Ip type monomers, 25 mmol functionality) is added and stirred mechanically for 4 hours at RT. The suspension is filtered and washed with $Et_2O$ and ice-water. The wet sorbent is suspended in 15 M HCl (100 mL) and stirred mechanically for 30 minutes. The suspension is filtered and the sorbent is washed with water. Next the sorbent is suspended in water (250 mL) and mechanically stirred for 12 hours at 100° C. Afterwards the suspension is filtered, washed with water and dried overnight over $P_2O_5$ under vacuum.

3.4 Preparation of poly(ninhydrine) Based on poly(indene)

Similar to a known procedure (B. Liu, F. Jin, et al., Angew. Chem., Int. Ed. 56(41) (2017) 12712-12717) in a glass reactor equipped with mechanical stirrer sorbent containing indene functionality (Ii-type monomer, 5 mmol functionality) is suspended in EtOH (20 mL). Next $FeCl_2$ (0.5 mmol) and polymethylhydrosiloxane (15 mmol) are added to the suspension and the mixture is heated to 80° C. under air atmosphere for 6 hours under continuous mechanical stirring. The mixture is cooled to RT and KF (15 mmol) was added to the suspension and is stirred for 1 hour. The suspension is filtered over a 200 µm filter and washed with water and acetone and dried overnight over $P_2O_5$ under vacuum.

Example 4—Analysis of Sorbents

General Methods for Determining Urea Binding Capacity

Figure 4A:
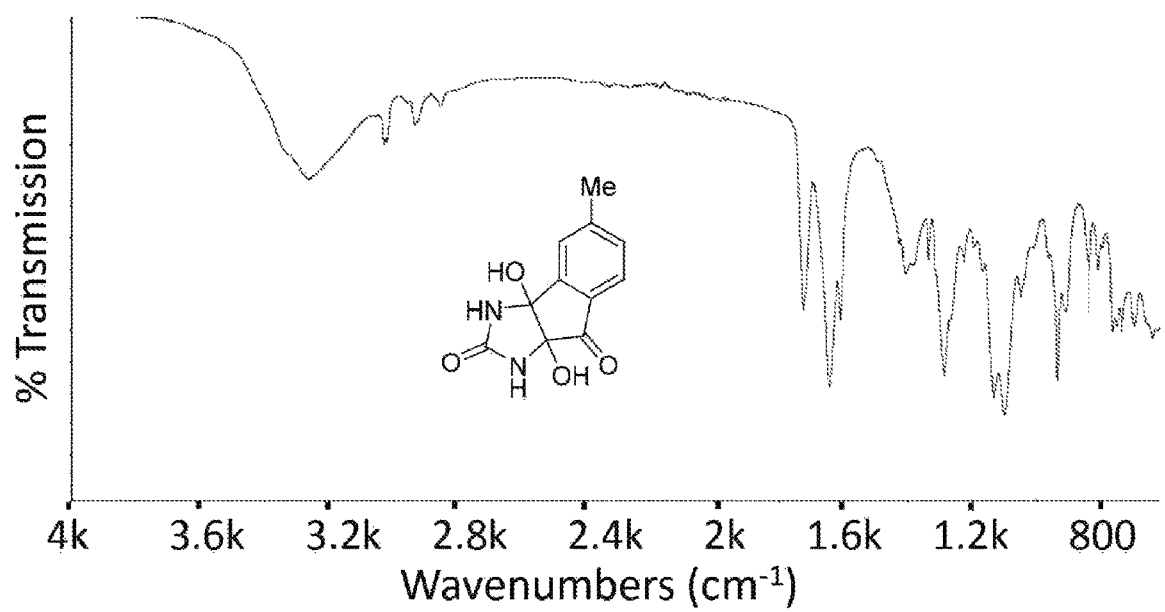
FIG. 4—FTIR spectroscopic analysis of urea bound to a sorbent. A) reference spectrum of urea bound to methylninhydrin shows a characteristic signal in the 1700 $cm^{-1}$ region, which is notably different from the spectrum of FIG.
Figure 4B:
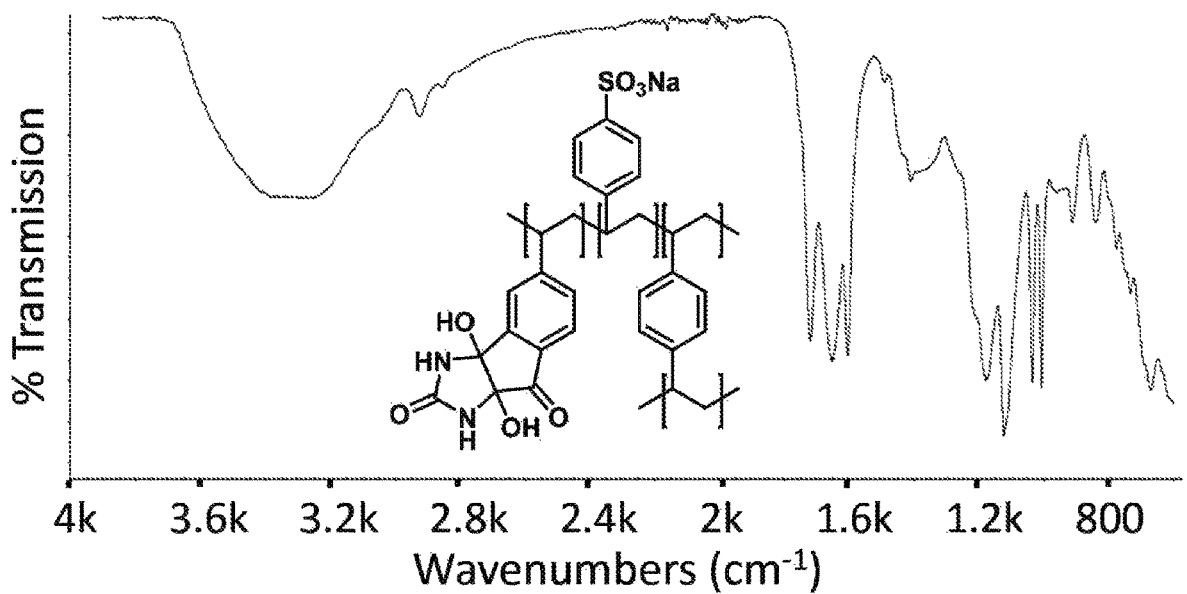

Sorbent (10 mg or 15 mg) was suspended in urea-enriched PBS (30 mM, 1 mL or 1.5 mL) in a 1.5 mL microcentrifuge tube (Eppendorf, individual tube for each timepoint) and placed at 37° C. for a set amount of time. The sorbent was spun down in the tube (12.000 rpm in a conventional benchtop centrifuge, 5 min) and the urea concentration was determined in the supernatant using a commercially available urease assay (Urea CT* FS** colorimetric test purchased at DiaSys Diagnostic Systems GmbH, Holzheim, Germany). In brief, this test determines urea concentrations via a coupled enzyme reaction, which results in a colorimetric (570 nm) product in a concentration proportional to the urea concentration. To determine the maximum urea binding capacity a sample was placed at 70° C. for 24 hours and the urea concentration was determined in the supernatant. FIG. 4 shows FTIR analysis of bound urea.

In an alternate method, sorbent (15 mg) was suspended in a solution of urea in PBS (1.5 mL, 30 mM or 50 mM) in a 1.5 mL Eppendorf and were placed in a rotation oven at 70° C. After 24 hours the sample was allowed to cool to RT and the urea concentration was determined in the supernatant by a standard urease assay (a urea stock solution kept for 24 hours at 70° C. was used as a negative control). The urea binding capacity of the sorbent was calculated based on the difference in urea concentration of the supernatant of the sorbent and the control solution.

4.1 Analysis of the Effect of the Duration of the Conversion Reaction

To determine the time needed to fully oxidize the indanone groups, different batches of the polymers listed in table 2 were oxidized for 1, 8, or 24 hours, after which the maximum urea binding capacity was determined. Based on these results it was determined that the oxidation likely goes to completion between 8 and 24 hours.

TABLE 2 urea binding capacity as a function of conversion duration

| Duration of conversion (in hours) | Feed ratio (vinylindanone:styrene sulfonate) | |
| --- | --- | --- |
| | 100:0 | 60:40 |
| | Urea binding capacity (mmol/g) | |
| 1 | 0.59 | 0.76 |
| 8 | 1.32 | 1.48 |
| 24 | 1.43 | 1.65 |

4.2 Analysis of the Effect of the Amount of Hydrophilic Comonomer

Maximum urea binding capacities were determined for sorbents with different feed composition ratios (ninhydrin:styrene sulfonate), and are shown in table 3. NMR and solid state NMR analysis of the resulting sorbents showed that sorbent composition is close to feed composition.

TABLE 3 urea binding capacity as a function of hydrophilic comonomer content

| Feed ratio (ninhydrin:styrene sulfonate) | Urea binding capacity (mmol/g) |
| --- | --- |
| 100:0 | 1.43 |
| 90:10 | 1.68 |
| 80:20 | 1.74 |
| 70:30 | 1.70 |
| 60:40 | 1.65 |
| 40:60 | 1.17 |
| 20:80 | 0.57 |
| 0:100 | 0 |

4.3 Analysis of Waste Solute Binding in More Complex Mixtures

Sorbent (10 mg) with a 70:30 feed ratio of ninhydrin:styrene sulfonate was suspended in a creatinine- and urea-enriched PBS (0 to about 30 mM, 1000 µL) in a 1.5 mL microcentrifuge tube (Eppendorf) and placed at 37° C. for 16 hours. The sorbent was spun down in the tube (15.000 rpm in a conventional benchtop centrifuge, 15 min) and the creatinine and urea concentrations were determined in the supernatant. Table 4 shows the results.

TABLE 4 creatinine and urea binding capacity in mixtures

| Creatinine (mM) | | Urea (mM) | | Sorbed in 16 h (mmol/g) | |
|---|---|---|---|---|---|
| T = 0 h | T = 16 h | T = 0 h | T = 16 h | Creatinine | Urea |
| 11.0 | 6.2 | 0 | 0 | 0.48 | — |
| 0 | 0 | 31.5 | 25.3 | — | 0.62 |
| 11.3 | 6.9 | 32 | 26.4 | 0.44 | 0.56 |

4.4 Amino Acids as Nucleophilic Waste Solutes

Sorbent (5 mg) with a 70:30 feed ratio of ninhydrin:styrene sulfonate was suspended in tryptophan-enriched PBS (10 mM, 500 μL) in a 1.5 mL microcentrifuge tube (Eppendorf) and placed at 37° C. for 16 hours. The sorbent was spun down in the tube (15.000 rpm in a conventional benchtop centrifuge, 15 min) and the tryptophan concentration was determined in the supernatant by UV absorption at 280 nm and compared with a control (for which the same procedure was used, using non-enriched PBS instead). The tryptophan concentration dropped from 10 mM to 3.0 mM in 16 hours and the suspension of sorbent in PBS turned purple, indicating the formation of Ruhemann's purple.

4.5 Urea Binding Capacity of Further Sorbents

For sorbents prepared according to the indicated methods in table 5, experiments were performed (in duplo) to determine their urea binding capacity, using the alternate method described above. Average binding capacity is reported in Table 5.

TABLE 5

Urea binding capacity of further sorbents

| # | Proc. | Monomer | Inert solvent | Crosslinker % | Result | BC (mmol/g) |
|---|---|---|---|---|---|---|
| 1 | 2.3 | li | ShellSolTD:Toluene 4:1 | 3 | Powder | 2.0 |
| 2 | 2.3 | li | Heptane:Toluene 4:1 | 3 | Powder | 2.2 |
| 3 | 2.3 | li | Heptane:Toluene 1:1 | 3 | Powder | 2.1 |
| 4 | 2.3 | li | Toluene | 3 | Beads | 2.7 |
| 5 | 2.3 | li | Toluene | 6 | Beads | 2.8 |
| 6 | 2.3 | li | Toluene:Nitrobenzene 1:1 | 3 | Beads | 2.9 |
| 7 | 2.2 | ln | None | 50 | Powder | 1.0 |
| 8 | 2.2 | ln | None | 67 | Powder | 0.74 |
| 9 | 2.2 | ln | None | 80 | Powder | 0.76 |
| 10 | 2.2 | li | None | 50 | Powder | 0.43 |
| 11 | 2.2 | li | None | 67 | Powder | 0.33 |
| 12 | 2.2 | li | None | 80 | Powder | 0.30 |
| 13 | 2.2 | lp | None | 50 | Powder | |
| 14 | 2.2 | lp | None | 10 | Powder | |

Proc. denotes the procedure for sorbent preparation that was used, as described in example 2;
Crosslinker refers to divinylbenzene;
BC is urea binding capacity;
li refers to vinylindanone monomers;
ln refers to vinylninhydrine monomers;
lp refers to vinylphthalic ester monomers.

Example 5—Regeneration of Sorbents

Figure 5A:
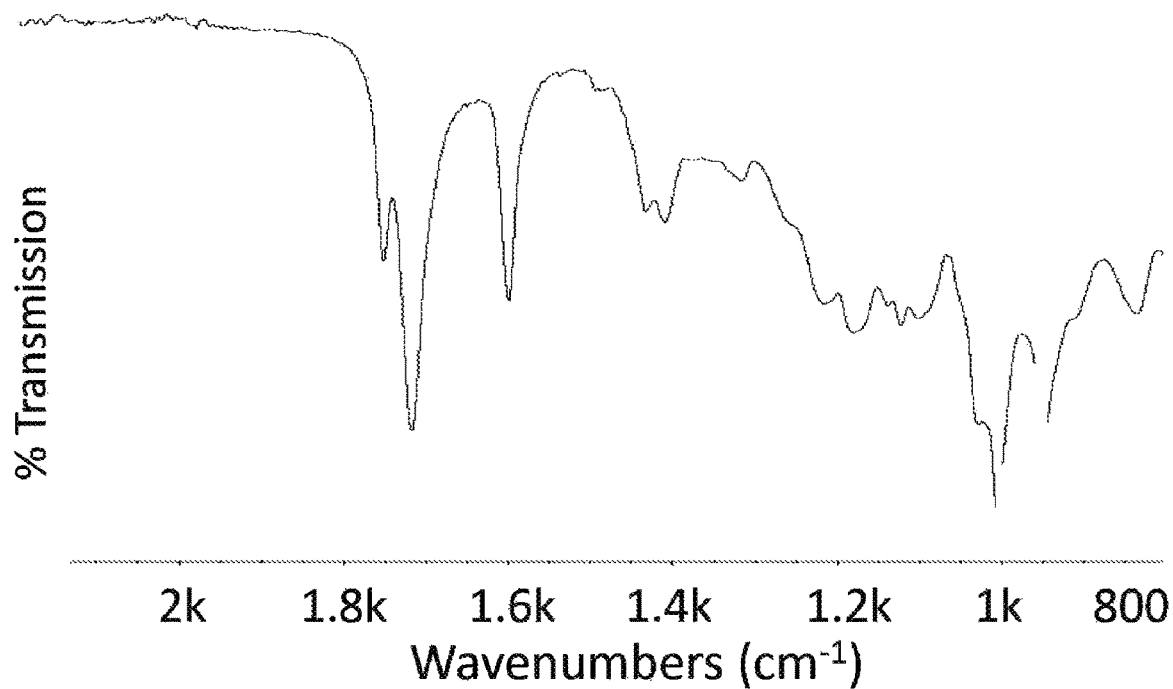
Figure 5B:
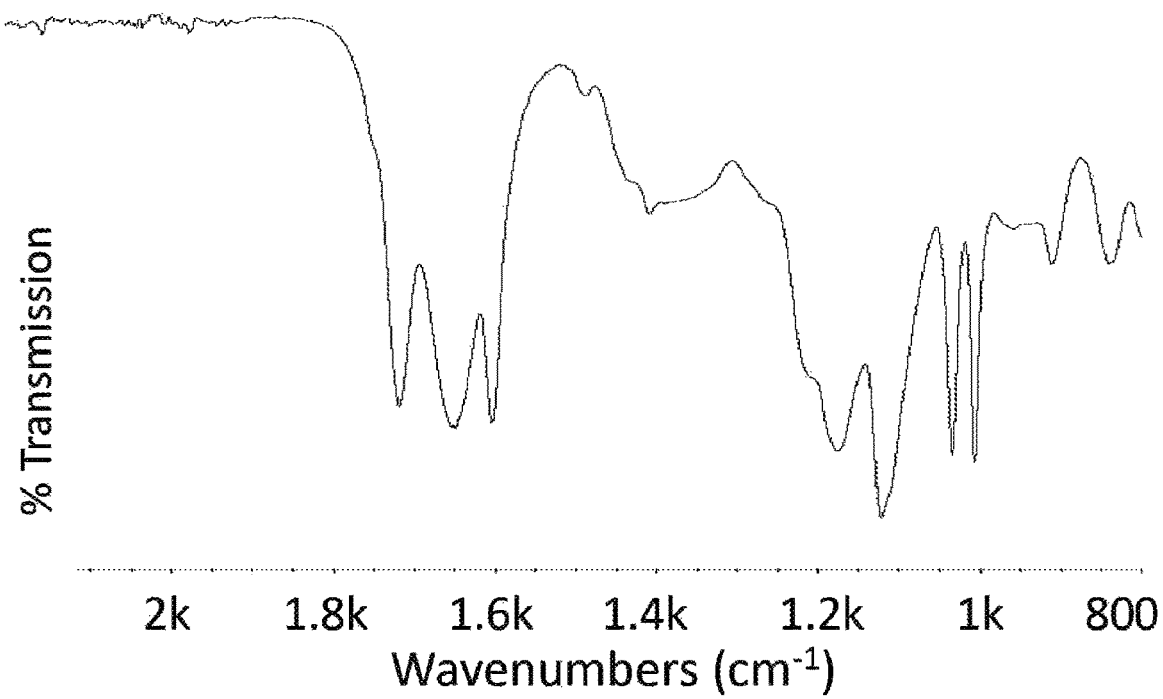

Sorbent with a 70:30 feed ratio of ninhydrin:styrene sulfonate that was previously saturated with bound urea (5 mg) was placed in HCl solutions in water (500 μL) of various concentrations, and placed in a rotating device (rollerbank) at 37° C. for 16 hours. The tubes were spun down (15.000 rpm, 15 min) and the pellets were freeze dried. The resulting sorbents were analysed by IR spectroscopy. FIG. 5 shows IR analysis of free, unloaded sorbent (FIG. 5A), of the sorbents after binding urea (FIG. 5B), of unsuccessful regeneration protocols (FIG. 5C), and of successful regeneration using either 12M HCl, or using three consecutive incubations with 6M HCl (FIG. 5D).

In a further experiment, sorbent saturated with urea (100 mg, urea binding capacity of 1.8 mmol/g) was placed in an acidic solution (2 mL) under the conditions indicated in table 6. Afterwards the supernatant was removed and the sorbent was washed with water until the pH was neutral. The urea binding capacity of the regenerated sorbent was determined.

TABLE 6 conditions used for regeneration and the corresponding new binding capacities

| Entry | Acid | Temp. (° C.) | Time (h) | Sorbent concentration (mg/mL) | New BC (mmol/g) | Regeneration (%) |
|---|---|---|---|---|---|---|
| 1 | 6M HCl | RT | 24 | 50 | 0.35 | 19 |
| 2 | 6M HCl | 50 | 24 | 50 | 0.50 | 28 |
| 3 | 6M HCl | 70 | 24 | 50 | 0.71 | 39 |
| 4 | 6M HCl | 70 | 24 + 24[a] | 50 | 0.83 | 46 |
| 5 | 6M HCl | 70 | 2 | 50 | 0.27 | 15 |
| 6 | 6M HCl | 70 | 4 | 50 | 0.37 | 21 |
| 7 | 6M HCl | 70 | 6 | 50 | 0.36 | 20 |
| 8 | 6M HCl | 70 | 8 | 50 | 0.40 | 22 |
| 9 | 1.8M $H_2SO_4$ | 70 | 24 | 50 | 0.35 | 19 |
| 10 | 3.6M $H_2SO_4$ | 70 | 24 | 50 | 0.46 | 25 |
| 11 | 9.2M $H_2SO_4$ | 70 | 24 | 50 | 0.41 | 23 |
| 12 | 6M AcOH | 70 | 24 | 50 | 0.1 | 7 |
| 13 | 6M HBr | 70 | 24 | 50 | 0.4 | 29 |
| 14 | 6M HBr | 70 | 24 | 15 | 0.6 | 45 |
| 15 | 3M HBr | 70 | 24 | 15 | 0.5 | 33 |
| 16 | 3M PCA | 70 | 24 | 15 | 0.5 | 36 |
| 17 | 6M PCA | 70 | 24 | 15 | 0.9 | 61 |
| 18 | 8M PCA | 70 | 24 | 15 | 0.7 | 46 |
| 19 | 10M PCA | 70 | 24 | 15 | 0 | 0 |
| 20 | 6M PCA | 70 | 24 | 7.5 | 1.0 | 69 |
| 21 | 6M PCA | 50 | 24 | 15 | 0.6 | 46 |
| 22 | 6M PCA | 70 | 6 | 15 | 0.9 | 64 |
| 23 | 6M PCA | 70 | 48 | 15 | 0.7 | 48 |

[a]The supernatant was refreshed after 24 h and placed in the oven again for another 24 h.

REFERENCES

Ashraf S. M. "A Laboratory Manual of Polymers" I. K. International Pvt Ltd, 8 Dec. 2008.

Becker and Russell, J. Org. Chem., 1963 DOI: 10.1021/jo01042a502

Evenepoel P, Bammens B, Verbeke K, Vanrenterghem Y. Kidney Int 2006; 70:794-9.

De Fijter C W, Oe P L, Nauta J J, et al. Adv Perit Dial 1991; 7:186-9.

Gardner et al., Appl Biochem Biotechnol. 1984; 10:27-40

Gotch F A. Kinetic modeling of continuous flow peritoneal dialysis. Semin Dial 2001; 14:378-83.

Katritzky et al., Chem. Rev. (2004) DOI: 10.1021/cr020750m

Perl J, Wald R, Bargman J M, et al. Clin J Am Soc Nephrol 2012; 7:1145-54.

Piraino B, Sheth H. Blood Purif 2010; 29:145-9.

Marminon et al., (2015, DOI: 10.1016/j.tetlet.2015.02.086

"Metal-Catalyzed Cross-Coupling Reactions" 2$^{nd}$ ed. (2008) DOI: 10.1002/9783527619535

Nesrallah G E et al., J Am Soc Nephrol 2012; 23:696-705.

Susantitaphong P et al., Am J Kidney Dis 2012; 59:689-99.

Ting G O, Kjellstrand C, Freitas T, Carrie B J, Zarghamee S. Am J Kidney Dis 2003; 42:1020-35.

EP121275A1/U.S. Pat. No. 4,897,200A/DE2305186A1/U.S. Pat. No. 3,933,753A/WO2004078797A1/U.S. Pat. No. 4,178,241A/WO2017116515A1/WO2011102807A1/WO2016126596

The invention claimed is:

1. Method for producing a ninhydrin-type sorbent, comprising the steps of:

i) providing a monomer of general formula (I):

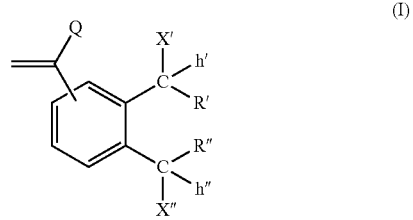

(I)

wherein the monomer of general formula (I) is of general formula (Ii), of general formula (Ip), or of general formula (In)

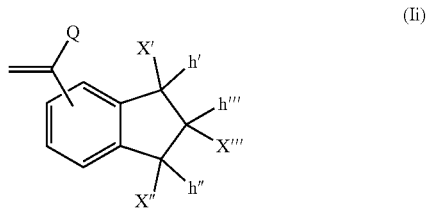

(Ii)

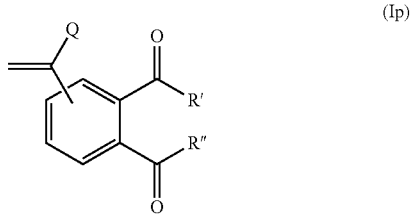

(Ip)

-continued (In)

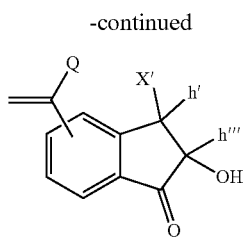

wherein:

Q is —H or —CH$_3$;

h' and h" are each independently absent or selected from a halogen and —H;

X' and X" are each independently selected from a halogen, —H, =O, =N—(CH$_2$)$_n$—H, —O—(CH$_2$)$_n$—H, —O—C(CH$_3$)$_3$, —O—CH(CH$_3$)$_2$, —(CH$_2$)$_n$—H, and —N(—[CH$_2$]$_n$—H)$_2$, wherein any —H is optionally replaced by a halogen, wherein each instance of n is independently selected from 0, 1, 2, 3, or 4, R' and R" are each independently selected from a halogen, —H, —OH, —O—(CH$_2$)$_n$—H, —O—C(CH$_3$)$_3$, —O—CH(CH$_3$)$_2$, —N(—[CH$_2$]$_n$H)$_2$, and —(CH$_2$)$_n$—H, wherein any —H is optionally replaced by a halogen, wherein each instance of n is independently selected from 0, 1, 2, 3, or 4, or wherein R' and R" together form a bridging moiety selected from —CH$_2$—, =CH—, —C(=O)—, —C(—OH)$_2$—, —C(—OH)$_2$—C(—OH)$_2$—, —O—, —NH—, and —C(h''')(X''')—, wherein h''' is independently selected as defined for h' or is —NH—C(=O)—NH$_2$;

X''' is independently selected as defined for X'; or wherein

X''' is —OH and h''' and one of h' or h" together form a bridging moiety —NH—C(=O)—NH—;

ii) polymerizing the provided monomer to obtain a polymer; and iii) converting polymerized monomers of general formula (I) that are not ninhydrin-type monomers into ninhydrin-type monomers.

2. The method according to claim 1, wherein the monomer of general formula (I) is selected from the group consisting of:

4-ethenylindene, 5-ethenylindene, 6-ethenylindene, 7-ethenylindene, 4-ethenylindane-1-one, 5-ethenylindane-1-one, 6-ethenylindane-1-one, 7-ethenylindane-1-one, 4-ethenylindane-1,2-dione, 5-ethenylindane-1,2-dione, 6-ethenylindane-1,2-dione, 7-ethenylindane-1,2-dione, 4-ethenylindane-2-one, 5-ethenylindane-2-one, 4-ethenylindane-1,3-dione, 5-ethenylindane-1,3-dione, 4-ethenylindane-1,2,3-trione, 5-ethenylindane-1,2,3-trione, 4-ethenyl-2,2-dihydroxyindane-1,3-dione, 5-ethenyl-2,2-dihydroxyindane-1,3-dione, 3-ethenylbenzene-1,2-dicarboxylic acid, 4-ethenylbenzene-1,2-dicarboxylic acid, dimethyl 3-ethenylbenzene-1,2-dicarboxylate, dimethyl 4-ethenylbenzene-1,2-dicarboxylate, diethyl 3-ethenylbenzene-1,2-dicarboxylate, diethyl 4-ethenylbenzene-1,2-dicarboxylate, 4-ethenyl-2-benzofuran-1,3-dione, 5-ethenyl-2-benzofuran-1,3-dione, 3a,8a-dihydroxy-7-ethenyl-1,3,3a,8a-tetrahydroindeno[1,2-d]imidazole-2,8-dione, 3a,8a-dihydroxy-6-ethenyl-1,3,3a,8a-tetrahydroindeno[1,2-d]imidazole-2,8-dione, 3a,8a-dihydroxy-5-ethenyl-1,3,3a,8a-tetrahydroindeno[1,2-d]imidazole-2,8-dione, and 3a,8a-dihydroxy-4-ethenyl-1,3,3a,8a-tetrahydroindeno[1,2-d]imidazole-2,8-dione.

3. The method according to claim 1, wherein the monomer of general formula (I) is selected from the group consisting of: 5-ethenylindene, 6-ethenylindene, 5-ethenylindane-1-one, 6-ethenylindane-1-one, 5-ethenylindane-1,3-dione, 5-ethenylindane-1,2,3-trione, 5-ethenyl-2,2-dihydroxyindane-1,3-dione, 4-ethenylbenzene-1,2-dicarboxylic acid, dimethyl 4-ethenylbenzene-1,2-dicarboxylate, diethyl 4-ethenylbenzene-1,2-dicarboxylate, 3 a, 8a-dihydroxy-6-ethenyl-1,3,3 a, 8a-tetrahydroindeno [1,2-d] imidazole-2,8-dione, and 3 a,8a-dihydroxy-5-ethenyl-1,3,3 a, 8a-tetrahydroindeno [1,2-d] imidazole-2,8-dione.

4. The method according to claim 1, wherein a comonomer is provided along with the monomer of general formula (I).

5. The method according to claim 1, wherein the polymer is crosslinked after polymerization or during polymerization.

6. The method according to claim 1, wherein in step iii) a conversion reaction is used comprising a step selected from the group consisting of:
a) oxidation;
b) halogenation;
c) alkylation;
d) fragmentation; and
e) hydrolysis.

7. The method according to claim 4, wherein the comonomer is selected from the group consisting of styrene, isopropenylbenzene, divinylbenzene, vinylbenzenesulfonic acid, acrylic acid, methacrylic acid, methyl acrylate, methyl methacrylate, 2-hydroxyethyl 2-methylprop-2-enoate (HEMA), 2-hydroxypropyl 2-methylprop-2-enotate, 2-hydroxyethyl prop-2-enoate, 2-hydroxypropyl prop-2-enotate, N-(2-hydroxyethyl)methacrylamide, N-(2-hydroxypropyl) methacrylamide N-(2-hydroxyethyl)acrylamide, N-(2-hydroxypropyl)acrylamide, a telechelic'-alkylenebisacrylamide, N-isopropylacrylamide (NIPAm), divinyl sulfone, and butadiene.

* * * * *